US007932376B2

(12) United States Patent
Douglass, III et al.

(10) Patent No.: US 7,932,376 B2
(45) Date of Patent: Apr. 26, 2011

(54) PYRIMIDINE-BASED NON-NUCLEOTIDE COMPOSITION AND METHOD FOR INHIBITING PLATELET AGGREGATION

(75) Inventors: James G. Douglass, III, Apex, NC (US); Paul S. Watson, Carrboro, NC (US); Sammy R. Shaver, Chapel Hill, NC (US); Krzysztof Bednarski, Springville, UT (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 1210 days.

(21) Appl. No.: 11/413,600

(22) Filed: Apr. 28, 2006

(65) Prior Publication Data

US 2006/0258614 A1 Nov. 16, 2006

Related U.S. Application Data

(60) Provisional application No. 60/678,890, filed on May 5, 2005.

(51) Int. Cl.
  *C07H 19/06* (2006.01)
  *C07H 19/067* (2006.01)
  *C07D 239/47* (2006.01)
  *A61K 31/7068* (2006.01)
  *A61K 31/506* (2006.01)
  *A61P 7/02* (2006.01)
(52) U.S. Cl. ......... 536/26.8; 514/49; 514/269; 544/309; 544/317
(58) Field of Classification Search .................. 536/26.8; 544/309, 317; 514/49, 269
  See application file for complete search history.

(56) References Cited

U.S. PATENT DOCUMENTS

| 3,321,463 | A | 5/1967 | Moffatt et al. | |
| 4,794,174 | A | 12/1988 | Secrist, III | 536/26 |
| 5,049,550 | A | 9/1991 | Zamecnik | 514/47 |
| 5,681,823 | A | 10/1997 | Kim et al. | 514/47 |
| 5,747,496 | A | 5/1998 | Cox et al. | 514/258 |
| 6,037,343 | A | 3/2000 | Ali | 514/252 |
| 6,040,317 | A | 3/2000 | Duggan et al. | 514/317 |
| 6,297,232 | B1 | 10/2001 | Bonnert et al. | 514/211.03 |
| 6,369,064 | B1 | 4/2002 | Brown et al. | 514/258 |

FOREIGN PATENT DOCUMENTS

| WO | WO 98/28300 A1 | 7/1998 |
| WO | WO 99/05142 A1 | 2/1999 |
| WO | WO 99/05143 A1 | 2/1999 |
| WO | WO 99/05144 A1 | 2/1999 |
| WO | WO 99/41254 A1 | 8/1999 |
| WO | WO 00/04021 A1 | 1/2000 |
| WO | WO 01/36438 A1 | 5/2001 |
| WO | WO 01/40243 A2 | 6/2001 |
| WO | WO 01/40246 A1 | 6/2001 |
| WO | WO 01/94368 A1 | 12/2001 |
| WO | WO 02/16381 A2 | 2/2002 |
| WO | WO 02/096428 A1 | 12/2002 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Tantry et al. Expert. Opin. Pharmacother., 6(12): 2027-2045, 2005.*
Rauch et al., Ann. Intern. Med. 134(3): 224-238, 2001.*
Van Aken et al., Clin. Appl. Thromb. Hemost., 7(3): 195-204, 2001.*
Awaya et al. JP4800579; CA 78: 72530, 1973( CAPLUS Abstract).*
Abstracts of Papers, 225TH ACS National Meeting; New Orleans, LA; Mar. 2003; MEDI-016.
André, et al., "P2Y$_{12}$ regulates platelet adhesion/activation, thrombus growth, and thrombus stability in injured arteries," *J. Clin. Invest.*, 112: 398-406 (2003).
Antiplatelet Trialists' Collaboration, "Collaborative overview of randomized trials of antiplatelet therapy Prevention of death, myocardial antiplatelet therapy in various categories of patients," *Br. Med. J.* 308: 81-106 (1994).
Antiplatelet Trialists' Collaboration, "Collaborative overview of randomized trials of antiplatelet therapy—II: Maintenance of vascular antiplatelet therapy," *Br. Med. J.* 308: 159-168 (1994).
Baraldi, et al., "Novel $N^6$-(Substituted-phenylcarbamoyl)adenosine-5'-uronamides as Potent Agonists for $A_3$ Adenosine Receptors," *Journal of Medicinal Chemistry* 39(3): 802-806 (1996).
Bennett, et al., "Thrombotic Thrombocytopenic Purpura Associated with Clopidogrel," *N. Engl. J. Med.* 342: 1771-1777 (2000).
Bennett, et al., "Thrombotic Thrombocytopenic Purpura Associated with Ticlopidine," *Ann. Intern. Med.* 128: 541-544 (1998).
Bernat, et al., "Effect of Various Antiplatelet Agents on Acute Arterial Thrombosis in the Rat," *Thromb. Haemostas.* 70: 812-826 (1993).
Brown, et al., "Matrix Metalloproteinase Inhibitors Containing a (Carboxyalkyl)amino Zinc Ligand: Modification of the P1 and P2' Residues," *J. Med. Chem.* 37(5): 674-688 (1994).
Bush, et al., "Effects of the selective thromboxane synthetase inhibitor dazoxiben on variations in cyclic blood flow in stenosed canine coronary arteries," *Circulation* 69: 1161-1170 (1984).
Camaioni, et al., "Adenosine Receptor Agonists: Synthesis and Biological Evaluation of the Diastereoisomers of 2-(3-Hydroxy-3-phenyl-1-propyn-1-yl)NECA," *Bioorganic & Medicinal Chemistry* 5(12): 2267-2275 (1997).

(Continued)

*Primary Examiner* — Venkataraman Balasubramanian
(74) *Attorney, Agent, or Firm* — Perkins Coie LLP; Viola T. Kung

(57) ABSTRACT

This invention is directed to a method of preventing or treating diseases or conditions associated with platelet aggregation. The method is also directed to a method of treating thrombosis or related disorders. The method comprises administering to a subject a pharmaceutical composition comprising an effective amount of a non-nucleotide pyrimidine-based compound, preferably a P2Y$_{12}$ receptor antagonist compound, wherein said amount is effective to inhibit platelet aggregation. The compounds useful for this invention include compounds of general Formulae I and Ia-Ic, or tautomers, salts, hydrates, and solvates thereof. The present invention also provides novel compounds of Formulae I and Ia-Ic.

22 Claims, No Drawings

OTHER PUBLICATIONS

Cristalli, et al., "2-Aralkynyl and 2-Heteroalkynyl Derivativse of Adenosine-5'-N-ethyluronamide as Selective $A_{2a}$ Adenosine Receptor Agonists," *Journal of Medicinal Chemistry* 38(9): 1462-1472 (1995).

Dangelmaier, et al., "Potentiation of Thromboxane $A_2$-induced Platelet Secretion by Gi Signaling through the Phosphoinositide-3 Kinase Pathway," *Thromb. Haemostas.* 85: 341-348 (2001).

The EPIC investigators; Califf, R.M. coordinating author; "Use of a Monoclonal Antibody Directed Against the Platelet Glycoprotein IIb/IIIa Receptor in High-Risk Coronary Angioplasty," *New Engl. J. Med.* 330: 956-961 (1994).

Folts, et al., "Platelet Aggregation in Partially Obstructed Vessels and its Elimination with Aspirin," *Circulation* 54: 365-370 (1976).

Frederick et al., "The Protective Dose of the Potent GPIIb/IIIa Antagonist SC-54701A is Reduced When Used in Combination with Aspirin and Heparin in a Canine Model of Coronary Artery Thrombosis," *Circulation* 93: 129-134 (1996).

Gachet, C., "ADP Receptors of Platelets and their Inhibition," *Thromb. Haemostas.* 86: 222-232 (2001).

Geiger, et al., "Specific Impairment of Human Platelet $P2Y_{AC}$ ADP Receptor-Mediated Signaling by the Antiplatelet Drug Clopidogrel," *Arterioscler. Thromb. Vasc. Biol.* 19: 2007-2011 (1999).

The GUSTO IIa investigators; "Randomized Trial of Intravenous Heparin Versus Recombinant Hirudin for Acute Coronary Syndromes," *Circulation* 90: 1631-1637 (1994).

Hass, et al., "A Randomized Trial Comparing Ticlopidine Hydrochloride with Aspirin for the Prevention of Stroke in High-Risk Patients," *N. Engl. J. Med.* 321: 501-507 (1989).

Hechler, of al., "A Role of the Fast ATP-gated $P2X_1$ Cation Channel in Thrombosis of Small Arteries In Vivo," *J. Exp. Med.* 198: 661-667 (2003).

Herbert, et al., "Inhibitory Effect of Clopidogrel on Platelet Adhesion and Intimal Proliferation After Arterial Injury in Rabbits," *Arterioscl. Thromb.* 13: 1171-1179 (1993).

Hourani, et al., "Effects of the $P_2$-purinoceptor antagonist, suramin, on human platelet aggregation induced by adenosine 5'-diphosphate," *Br. J. Pharmacology* 105: 453-457 (1992).

Humphries et al., "Pharmacological profile of the novel P2T-purinoceptor antagonist, FPL 67085 in vitro and in the anaesthetized rat in vivo," *Br. J. Pharmacol.* 115:1110-1116 (1995).

The IMPACT-II investigators; "Randomised placebo-controlled trial of effect of eptifibatide on complications of percutaneous coronary intervention: IMPACT-II," *Lancet* 349: 1422-1428 (1997).

Ingall, et al., "Antagonists of the Platelet $P_{2T}$ Receptor: A Novel Approach to Antithrombotic Therapy," *J. Med. Chem.* 42: 213-220 (1999).

Jacobson, et al., "Structure-Activity Relationships of 9-Alkyladenine and Ribose-Modified Adenosine Derivatives at Rat $A_3$ Adenosine Receptors," *Journal of Medicinal Chemistry* 38(10): 1720-12735 (1995).

Jagroop, et al., "Both the ADP receptors $P2Y_1$ and $P2Y_{12}$, play a roll in controlling shape change in human platelets," *Platelets* 14: 15-20 (2003).

Kapetanakis, et al., "Clopidogrel administration prior to coronary artery bypass grafting surgery: the cardiologist's panacea or the surgeon's headache?," *Eur. Heart J.* 26:576-83 (2005).

Lee, et al., "N-Alkoxysulfamide, N-Hydroxysulfamide, and Sulfamate Analogues of Methionyl and Isoleucyl Adenylates as Inhibitors of Methionyl-tRNA and Isoleucyl-tRNA Synthetases," *Bioorganic & Medicinal Chemistry Letters* 13(6): 1087-1092 (2003).

Lekstrom and Bell, "Aspirin in the Prevention of Thrombosis," *Medicine* 70: 161-177 (1991).

Lyga and Secrist III, "Synthesis of Chain-Extended and C-6' Functionalized Precursors of the Nucleoside Antibiotic Sinefungin," *Journal of Organic Chemistry* 48(12): 1982-1988 (1983).

Maffrand, et al., "ADP Plays a Key Role in Thrombogenesis in Rats," *Thromb. Haemostas.* 59: 225-230 (1988).

McKee, et al., "Aspirin Resistance in Cardiovascular Disease: A Review of Prevalence, Mechanisms, and Clinical Significance," *Thromb. Haemostas.* 88: 711-715 (2002).

Mickelson, et al., "Antiplatelet Antibody [7E3 F(ab$^1$)$_2$] Prevents Rethrombosis After Recombinant Tissue-Type Plasminogen Activator-Induced Coronary Artery Thrombolysis in a Canine Model," *Circulation* 81: 617-627 (1990).

Mitsunobu, O., "The Use of Diethyl Azodicarboxylate and Triphenylphosphine in Synthesis and Transformation of Natural Products," *Synthesis* 1-28 (1981).

Neuhaus, et al., "Safety Observations from the Pilot Phase of the Randomized r-Hirudin for Improvement of Thrombolysis (HIT-III) Study," *Circulation*, 90: 1638-1642 (1994).

Quinn and Fitzgerald, "Ticlopidine and Clopidogrel," *Circulation* 100: 1667-1672 (1999).

The RESTORE investigators; "Effects of Platelet Glycoprotein IIb/IIIa Blockade with Tirofiban on Adverse Cardiac Events in Patients with Unstable Angina or Acute Myocardial Infarction Undergoing Coronary Angioplasty," *Circulation* 96: 1445-1453 (1997).

Romson, et al., "Electrical induction of coronary artery thrombosis in the ambulatory canine: a model for in vivo evaluation of antithrombotic agents," *Thromb. Res.* 17(6):841-853 (1980).

Santosh and Balasubramanian, "A Facile and Stereoselective Synthesis of Arylethers of Vicinal Bromohydrins by Mitsunobu Reaction," *Synthetic Communications*, 24(8): 1049-1062 (1994).

Savi, et al., "Identification and Biological Activity of the Active Metabolite of Clopidogrel," *Thromb. Haemostas.* 84: 891-896 (2000).

Secrist III and Talekar, "5'-C-Chain-extended Adenosine Derivatives Related to Sinefungin, Synthesis and Biological Activity," *Nucleosides & Nucleotides* 9(4): 619-627 (1990).

Shebuski, et al., "Acceleration of Recombinant Tissue-Type Plasminogen Activator-Induced Thrombolysis and Prevention of Reocclusion by the Combination of Heparin and the Arg-Gly-Asp-Containing Peptide Bitistatin in a Canine Model of Coronary Thrombosis," *Circulation* 82: 169-177 (1990).

The TIMI 9a investigators; "Hirudin in Acute Myocardial Infarction," *Circulation* 90: 1624-1630 (1994).

Tschopp, et al., *Coron. Artery Dis.* 4: 809-817 (1993).

Weber, et al., "Low-Dose Aspirin Versus Anticoagulants for Prevention of Coronary Graft Occlusion,"*Am. J. Cardiol* 66: 1461-1468 (1990).

Hatanaka et al., "Preparation of cytidine analogs and CMP-sialic acid analogs", 2006 ACS on STN (Abstract); Accession No. 1993:449839 CAPLUS, Document No. 119:49839; Compounds CAS#s 146759-54-8 and 146759-55-9; Japanese Kokai Tokkyo Koho, Japan.

\* cited by examiner

PYRIMIDINE-BASED NON-NUCLEOTIDE COMPOSITION AND METHOD FOR INHIBITING PLATELET AGGREGATION

The present application claims the priority to U.S. Provisional Application No. 60/678,890, filed May 5, 2005; the content of which is incorporated herein by reference in its entirety.

TECHNICAL FIELD

This invention relates to pyrimidine-based non-nucleotide compounds and methods of making and using such compounds in the prevention or treatment of diseases or conditions associated with platelet aggregation, including thrombosis, stroke and myocardial infarction in humans and other mammals, and for inhibition of platelet aggregation in blood and blood-related products.

BACKGROUND OF THE INVENTION

Hemostasis is the spontaneous process of arresting bleeding from damaged blood vessels. Upon injury, precapillary vessels contract within seconds, and thrombocytes, or blood platelets, bind to the exposed subendothelial matrix of an injured vessel by a process called platelet adhesion. Platelets also stick to each other in a phenomenon known as platelet aggregation to form stable platelet aggregates that quickly help stop or slow blood outflow from injured vessels.

An intravascular thrombus can result from pathological disturbances of hemostasis, or by the rupture of atherosclerotic plaques. Platelet adhesion and aggregation are critical events in intravascular thrombosis. Activated under conditions of high shear blood flow in diseased vessels or by the release of mediators from other circulating cells and damaged endothelial cells lining the vessel, platelets and other cells accumulate at a site of vessel injury to form a thrombus, and recruit more platelets to the developing thrombus. The thrombus can grow to sufficient size to block off arterial blood vessels. Thrombi can also form in areas of stasis or slow blood flow in veins. Venous thrombi can easily detach portions of themselves, creating emboli that travel through the circulatory system. This process can result in blockade of other vessels, such as pulmonary arteries. Blockages of this sort can result in pathological outcomes such as pulmonary embolism. Thus, arterial thrombi cause serious disease by local blockade, whereas the morbidity and mortality associated with venous thrombi arise primarily after distant blockade, or embolization. Conditions associated with pathological thrombus formation include venous thromboembolism, thrombophlebitis, deep vein thrombosis, arterial embolism, coronary and cerebral arterial thrombosis, unstable angina, myocardial infarction, stroke, transient ischemic attack, cerebral embolism, renal embolism and pulmonary embolism.

A number of converging pathways lead to platelet aggregation. Whatever the initial stimulus, the final common event is crosslinking of platelets by binding of fibrinogen to a membrane binding site, glycoprotein IIb/IIIa (GP IIb/IIIa, also known as integrin $\alpha_{IIb}\beta_3$). Antagonists of the GP IIb/IIIa receptor have been shown to produce potent antithrombotic effects (Ali, U.S. Pat. No. 6,037,343; Duggan, et al., U.S. Pat. No. 6,040,317). GP IIb/IIIa antagonists include function-blocking antibodies like Abciximab (ReoPro®), cyclic peptides and peptidomimetic compounds (The EPIC investigators; Califf, R. M., coordinating author, *New Engl. J. Med.* 330: 956-961 (1994); The IMPACT-II investigators, *Lancet* 349:1422-1428 (1997); The RESTORE investigators, *Circulation* 96: 1445-1453 (1997)). The clinical efficacy of some of these newer drugs, such as Abciximab, is impressive, but recent trials have found that these approaches are associated with an increased risk of major bleeding, sometimes necessitating blood transfusion (The EPIC investigators; Califf, R. M., coordinating author, *New Engl. J. Med.* 330: 956-961 (1994)). Also, administration of this class of antiplatelet agent appears to be limited to intravenous methods.

Thrombin can produce platelet aggregation independently of other pathways but substantial quantities of thrombin are unlikely to be present without prior activation of platelets by other mechanisms. Thrombin inhibitors, such as hirudin, are highly effective antithrombotic agents. However, functioning as both antiplatelet and anti-coagulant agents, thrombin inhibitors again may produce excessive bleeding (The TIMI 9a Investigators, *Circulation*, 90: 1624-1630 (1994); The GUSTO IIa Investigators, *Circulation*, 90: 1631-1637 (1994); Neuhaus, et al., *Circulation*, 90: 1638-1642 (1994)).

Various antiplatelet agents have been studied as inhibitors of thrombus formation. Some agents such as aspirin and dipyridamole have come into use as prophylactic antithrombotic agents, and others have been the subjects of clinical investigations. To date, therapeutic agents such as the disintegrins, and the thienopyridines ticlopidine (TICLID®) and clopidogrel (PLAVIX®) have been shown to have utility as platelet aggregation inhibitors, although they can produce a substantial number of side effects and have limited effectiveness in some patients. (Hass, et al., *N. Engl. J. Med.*, 321: 501-507 (1989); Weber, et al., *Am. J. Cardiol.* 66: 1461-1468 (1990); Lekstrom and Bell, *Medicine* 70: 161-177 (1991)). In particular, the use of the thienopyridines in antiplatelet therapies has been shown to increase the incidence of potentially life threatening thrombotic thrombocytopenic purpura (Bennett, et al., *N. Engl. J. Med*, 342: 1771-1777 (2000)). Aspirin, which has a beneficial effect on the inhibition of platelet aggregation (Antiplatelet Trialists' Collaboration, *Br. Med. J.* 308: 81-106 (1994); Antiplatelet Trialists' Collaboration, *Br. Med. J.* 308: 159-168 (1994)), acts by inhibiting the synthesis of prostaglandins. Its well-documented, high incidence of gastric side effects, however, limits its usefulness in many patients. In addition, aspirin resistance has been observed in some individuals (McKee, et al., *Thromb. Haemost.* 88: 711-715 (2002)).

Many studies have demonstrated that adenosine 5'-diphosphate (ADP) plays a key role in the initiation and progression of arterial thrombus formation (Bemat, et al., *Thromb. Haemostas.* 70: 812-826 (1993)); Maffrand, et al., *Thromb. Haemostas.* 59: 225-230 (1988); Herbert, et al., *Arteriosc. Thromb.* 13: 1171-1179 (1993)). ADP induces inhibition of adenylyl cyclase and modulation of intracellular signaling pathways such as activation of phosphoinositide-3 kinase (PI3K), influx and mobilization of intracellular $Ca^{+2}$, secretion, shape change, and platelet aggregation (Dangelmaier, et al. *Thromb Haemost.* 85: 341-348 (2001)). ADP-induced platelet aggregation is triggered by its binding to specific receptors expressed in the plasma membrane of the platelet. There are at least three different P2 receptors expressed in human platelets: $P2X_1$, $P2Y_1$, and $P2Y_{12}$. The $P2X_1$ receptor is a ligand-gated cation channel that is activated by ATP, resulting in a transient influx of extracellular calcium. This receptor has been implicated in the regulation of platelet shape change, and recent evidence suggests its participation in thrombus formation in small arteries under high shear forces. (Jagroop, et al., *Platelets* 14:15-20 (2003); Hechler, et al., *J. Exp. Med.* 198: 661-667 (2003)). The $P2Y_1$ receptor is a G protein-coupled receptor that is activated by ADP, and is responsible for calcium mobilization from intracellular stores, platelet shape change and initiation of aggregation. The $P2Y_{12}$ receptor, also referred to as the $P^2Y_{ac}$ and $P2_T$ receptor, is a G protein-coupled receptor that is activated by ADP and is responsible for inhibition of adenylyl cyclase and activation of PI3K. Activation of $P2Y_{12}$ is required for platelet secretion and stabilization of platelet aggregates (Gachet, *Thromb. Haemost.* 86: 222-232 (2001); Andre, et al., *J. Clin. Invest.*, 112: 398-406 (2003)).

ADP-induced platelet aggregation requires the simultaneous activation of both $P2Y_1$ and $P2Y_{12}$ receptors, and therefore, aggregation can be inhibited by blockade of either receptor. Several authors have demonstrated that ADP-induced aggregation is inhibited in a concentration-dependent manner by analogues of adenosine triphosphate (ATP). ATP, itself, is a weak and nonselective, but competitive, $P2Y_1$ and $P2Y_{12}$ receptor antagonist. Ingall, et al. (*J. Med. Chem.* 42: 213-220 (1999)) have reported that modification of the polyphosphate side chain of ATP along with substitution of the adenine moiety at the $C^2$-position, resulted in compounds that inhibited the $P2_T$ receptor (or $P2Y_{12}$ receptor). Zamecnik (U.S. Pat. No. 5,049,550) has disclosed a method for inhibiting platelet aggregation by administration of a diadenosine tetraphosphate-like compound, App(CH$_2$)ppA. Kim and Zamecnik (U.S. Pat. No. 5,681,823) have disclosed $P^1$, $P^4$-(dithio)-$P^2$, $P^3$-(monochloromethylene)-5',5'''-diadenosine-$P^1$, $P^4$-tetraphosphate as an antithrombotic agent.

Nucleotide $P2Y_{12}$ antagonists have been developed, however, there is still a need for compounds that have improved oral bioavailability and blood stability.

Thienopyridines, ticlopidine and clopidogrel react covalently with the $P2Y_{12}$ receptor and produce irreversible platelet inhibition in vivo (Quinn and Fitzgerald, *Circulation* 100: 1667-1672 (1999); Geiger, et al., *Arterioscler. Thromb. Vasc. Biol.* 19: 2007-2011 (1999); Savi, et al., *Thromb Haemost.* 84: 891-896 (2000)). Patients treated with thienopyridines usually require 2-3 days of therapy to observe significant inhibition of platelet aggregation, however, and maximal inhibition usually is observed between 4 to 7 days after initiation of treatment. Also, the platelet inhibitory effect of thienopyridines persists up to 7-10 days after the therapy is discontinued, and both ticlopidine and clopidogrel produce a significant prolongation of the bleeding time (from 1.5 to 2-fold over control). Because of the prolonged effect of thienopyridines, these drugs need to be discontinued for 7 to 10 days prior to elective surgery, leaving the patient unprotected from a possible thrombotic event during that period. Recently, the association of thienopyridine treatment with events of thrombotic thrombocytopenic purpura has been reported (Bennett, et al., *N. Engl. J. Med.* 342: 1773-1777 (2000); Bennett, et al., *Ann. Intern. Med.* 128: 541-544 (1998)).

Derivatives of 5,7-disubstituted-1,2,3-triazolol[4,5-d]pyrimidin-3-yl-cyclopentanes and -tetrahydrofurans have been disclosed as antagonists of the P2T-(or $P2Y_{12}$) receptor on platelets (Cox, et al., U.S. Pat. No. 5,747,496, and related patents; Bonnert, et al., U.S. Pat. No. 6,297,232; WO 98/28300; Brown, et al., WO 99/41254; WO 99/05144; Hardern, et al. WO 99/05142; WO 01/36438; and Guile, et al. WO 99/05143) for use in the treatment of platelet aggregation disorders.

Guile, et al. (WO 00/04021) disclose the use of triazolo[4, 5-d]pyrimidine compounds in therapy. Brown, et al. (U.S. Pat. No. 6,369,064) disclose the use of triazolo(4,5-d)pyrimidine compounds in the treatment of myocardial infarction and unstable angina. Dixon, et al. (WO 02/096428) disclose the use of 8-azapurine derivatives in combination with other antithrombotic agents for antithrombotic therapy. Springthorpe discloses AZD6140 as a potent, selective, orally active $P2Y_{12}$ receptor antagonist which is now in Phase I clinical trials (Abstracts of Papers, 225$^{th}$ ACS National Meeting, New Orleans, La.; March, 2003; MEDI-016). WO 02/016381 discloses a method of preventing or treating diseases or conditions associated with platelet aggregation using mononucleoside polyphosphates and dinucleoside polyphosphates.

There is still a need in the areas of cardiovascular and cerebrovascular therapeutics, and in blood product preparation, purification, and storage, for selective, reversible inhibitors of platelet activation, which can be used in the prevention and treatment of thrombi or other aggregation-related problems.

SUMMARY OF THE INVENTION

This invention is directed to methods of preventing or treating diseases or conditions associated with platelet aggregation or where the aggregation of platelets inhibits treatment options. This invention is directed to methods of preventing or treating thrombosis and related disorders. This invention is further directed to methods of inhibiting platelet aggregation in blood and blood products comprising platelets, such as stored blood.

The method comprises administering to a mammalian subject or to a sample comprising blood or platelet-comprising material, a composition comprising one or more non-nucleotide $P2Y_{12}$ receptor antagonist compound that effectively binds to $P2Y_{12}$ receptors on platelets, preferably in a reversible manner, and thereby causes a inhibition of the ADP-induced platelet aggregation response in blood or in a platelet-comprising material. The compounds useful for this invention are compounds of general Formula I, and/or tautomers thereof, and/or pharmaceutically-acceptable hydrates, solvates, and/or salts thereof.

The invention also provides novel compounds and pharmaceutical compositions. The compounds of Formulae I, and Ia-c are useful in that they possess antagonist activity at platelet $P2Y_{12}$ receptors.

Optionally, the compounds of this invention can be used in combination with other compounds useful for the treatment of platelet aggregation disorders or diseases.

DETAILED DESCRIPTION OF THE INVENTION

Definitions

When present, unless otherwise specified, the following terms are generally defined as, but are not limited to, the following:

Halo substituents are taken from fluorine, chlorine, bromine, and iodine.

Alkyl groups are from 1 to 12 carbon atoms inclusively, either straight chained or branched, are more preferably from 1 to 8 carbon atoms inclusively, and most preferably 1 to 6 carbon atoms inclusively.

Alkylene chains are from 2 to 20 carbon atoms inclusively, have two points of attachment to the to the molecule to which they belong, are either straight chained or branched, can contain one or more double and/or triple bonds, are more preferably from 4 to 18 atoms inclusively, and are most preferably from 6 to 14 atoms inclusively.

Alkenyl groups are from 1 to 12 carbon atoms inclusively, either straight or branched containing at least one double bond but can contain more than one double bond.

Alkynyl groups are from 1 to 12 carbon atoms inclusively, either straight or branched containing at least one triple bond but can contain more than one triple bond, and additionally can contain one or more double bonded moieties.

"Alkoxy" refers to the group alkyl-O— wherein the alkyl group is as defined above including optionally substituted alkyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl-groups preferably having from 1 to 6 carbon atoms in the alkenyl moiety and from 6 to 10 carbon atoms inclusively in the aryl moiety.

"Arylalkynyl" refers to aryl-alkynyl-groups preferably having from 1 to 6 carbon atoms inclusively in the alkynyl moiety and from 6 to 10 carbon atoms inclusively in the aryl moiety.

"Aryloxy" refers to the group aryl-O-wherein the aryl group is as defined above including optionally substituted aryl groups as also defined above.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl-groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Heteroaryl" refers to a monovalent aromatic carbocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl-groups preferably having from 1 to 6 carbon atoms inclusively in the alkyl moiety and from 6 to 10 carbon atoms inclusively in the heteroaryl moiety. Such arylalkyl groups are exemplified by pyridylmethyl and the like.

"Heteroarylalkenyl" refers to heteroaryl-alkenyl-groups preferably having from 1 to 6 carbon atoms inclusively in the alkenyl moiety and from 6 to 10 carbon atoms inclusively in the heteroaryl moiety.

"Heteroarylalkynyl" refers to heteroaryl-alkynyl-groups preferably having from 1 to 6 carbon atoms inclusively in the alkynyl moiety and from 6 to 10 carbon atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Positions occupied by hydrogen in the foregoing groups can be further substituted with substituents exemplified by, but not limited to, hydroxy, oxo, nitro, methoxy, ethoxy, alkoxy, substituted alkoxy, fluoro, chloro, bromo, iodo, methyl, ethyl, propyl, butyl, alkyl, substituted alkyl, thio, thioalkyl, acyl, carboxyl, alkoxycarbonyl, carboxamido, substituted carboxamido, alkylsulfonyl, alkylsulfinyl, alkylsulfonylamino, sulfonamido, substituted sulfonamide, cyano, amino, substituted amino, acylamino, trifluoromethyl, trifluoromethoxy, phenyl, aryl, substituted aryl, pyridyl, imidazolyl, heteroaryl, substituted heteroaryl, cyclopropyl, cyclobutyl, cyclopentyl, cyclohexyl, cycloalkyl, substituted cycloalkyl, pyrrolidinyl, piperidinyl, morpholino, and heterocycle; and preferred heteroatoms are oxygen, nitrogen, and sulfur. It is understood that where open valences exist on these substituents they can be further substituted with alkyl, cycloalkyl, aryl, heteroaryl, and/or heterocycle groups, and where multiple such open valences exist, these groups can be joined to form a ring, either by direct formation of a bond or by formation of bonds to a new heteroatom, preferably oxygen, nitrogen, or sulfur. It is further understood that the above subtitutions can be made provided that replacing the hydrogen with the substituent does not introduce unacceptable instability to the molecules of the present invention, and is otherwise chemically reasonable.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

Tautomers are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

Solvates are addition complexes in which a compound of Formula I or II is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformnamide, N-methylacetamide, pyridine, dioxane, and diethyl ether. Hydrates are solvates in which the cosolvent is water. It is to be understood that the definition of compounds in Formulae I and II encompasses all possible hydrates and solvates, in any proportion, which possess the stated activity.

$P2Y_{12}$ Receptor Antagonist Compounds $P2Y_{12}$ receptor antagonist compounds useful for preventing or treating diseases or conditions associated with platelet aggregation and/or platelet activation include pyrimidine-based non-nucleotide compounds of general Formula I, and/or tautomers thereof, and/or pharmaceutically-acceptable tautomers, hydrates, solvates, and/or salts thereof:

Formula I wherein:

$R_1$ and $R_2$ are each independently selected from the group consisting of: hydrogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl (including saturation and/or unsaturation in the alkylene portion), aryl, heteroaryl, and saturated or unsaturated $C_{3-6}$ heterocycle; where all rings or chains optionally can bear one or more desired substituents; or $R_1$ and $R_2$ can be taken together to form a ring of 3 to 7 members, with or without substitution, and with or without heteroatoms in place of ring carbon atoms;

$R_3$ and $R_4$ are independently hydrogen, alkyl, halogen, alkenyl, substituted alkenyl, alkynyl, or substituted alkynyl.

$R_5$ is hydrogen, hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or $R_5$ is acylamino, provided that it incorporates an amino residue from the C-4 position of the pyrimidine;

$R_6$ is absent, or when $R_5$ has as its first atom N, $R_5$ and $R_6$ can be taken together to form a 5-membered fused imidazole ring (to give an etheno compound), optionally substituted on the etheno ring with one or more alkyl, cycloalkyl, aralkyl, or aryl moieties;

D is O or C;

V, Z, and Y are independently $CH_2$ (with or without substitution of H by alkyl groups or halogens), C=O (carbonyl), O, S, SO, $SO_2$, or NH (with or without substitution of H by an alkyl group or an acyl group); and when V and Z or Z and Y are both carbon, the linkage between the atom pair can be a saturated or unsaturated bond; or V, Z, and Y are independently absent;

X=H, —OR', —SR', —S(O)R', —S($O_2$)R', —$SO_3$H, —S($O_2$)NR'R", —NR'R", or —COOR', where R' and R" are independently H, a physiologically-relevant cation forming a carboxylate salt, alkyl, aryl, or aralkyl; or X is a group as provided in Formula II:

Formula II wherein:

$X_6$ is the attachment point to the moiety defined by V—Z—Y;

the ring defined by $X_1$-$X_6$ is taken to mean a ring with or without unsaturation; and $X_1$-$X_6$ are independently C, N, O, or S; and if any of $X_1$-$X_5$ is C, the carbon atom is optionally substituted with a variety of substituents such as halogen, alkyl, alkoxy, aminoalkyl, and the like; and if any of $X_1$-$X_5$ is N in an saturated ring, the nitrogen atom optionally bears substituents such as alkyl or acyl; or any of $X_1$-$X_5$ can be absent, with the proviso that at least two of $X_1$-$X_5$ are present, such that the ring described by $X_1$-$X_6$ consists of at least three atoms;

with the provisos that no two adjacent atoms $X_1$-$X_6$ are O—O or S—S and that the ring shown in Formula II contains no more than four heteroatoms, and that the shown pendant —$CO_2R_7$ unit in Formula II is a substituent on the ring described in Formula II, and that the ring of Formula II contains no halogen-group, hydroxy-group, sulfhydryl-group, or amino-group (—$NH_2$, N-substituted-amino, or N,N-disubstituted-amino) attached to an $sp^3$-hybridized-carbon atom that is bonded directly to a heteroatom selected from the group consisting of O, S, and N, as such types of compounds are unstable in many cases;

p=0,1 or 2;

r=0 or 1;

$R_7$ is H, a physiologically-relevant cation forming a carboxylate salt, alkyl, aryl, or aralkyl, with the resultant moiety C(=O)$OR_7$ preferably having an adjacent relationship to the attachment point of V; and M is H, halogen, alkyl, aminoalkyl, alkoxy, or acyl.

Preferably, the fliranosyl moiety in Formula I has the 2'- and 3'-oxygen-groups in a cis-orientation relative to one another on the faranose ring. Further, a furanosyl moiety which supports a 2',3'-acetal or -ketal group is, preferably, derived from ribose; other furanose derivatives can be used, however. A preferred stereochemical embodiment of this invention includes, but is not limited to (D)-ribose-(2', 3'-acetal or -ketal) compounds of Formula I.

In one embodiment of the present invention, when $R_a$ and $R_b$ are not identical, the compounds depicted in the following structures falling under the definitions of Formulae Ia-Ic represent either one of the two possible diastereomers (which arise from the resultant chiral carbon of the acetal) in pure form, or a mixture of the two diastereomers in any proportion. As a practical matter however, the compounds as depicted represent the pure forms of the diastereomers. Diastereomers are distinct compounds, each with potentially different chemical and biological properties; thus pure forms are preferred as pharmaceutical agents. In addition, there are generally reasons, including but not limited to, the ease of chemical synthesis or separation, chemical or biological stability, toxicity, pharmacokinetic or pharmacodynamic properties in living systems, and the like, to choose between the two possible isomers. While it is possible to resolve such diastereomeric mixtures using chiral chromatographic methods, more preferred is the synthesis of a single diastereomer.

Depending on the acetal in question, the synthesis of a single diastereomer can be achieved in several ways. In some cases, one diastereomer can be selectively generated over the other by carrying out the acetal-forming reaction at a low temperature (such as below 0° C., for example, from −10 to −30° C.). In other cases, a mixture of two diastereomers having different acetal stabilities can be subjected to aqueous acidic conditions, which leads to decomposition of the less-stable diastereomer, while leaving the more stable diastereomer intact. In general, the single diastereomer that survives the decomposition is preferred, since chemical stability is an important attribute for a pharmaceutical product. These principles are exemplified and illustrated in the following compound examples, but as they can be reasonably expanded to related structures; the specific example should not be taken as limiting.

A particularly useful embodiment is where the moiety defined by —C(O)OR$_7$ in Formula II comprises a —CO$_2$H group directly bonded to the ring in an ortho relationship to the atom defined by $X_6$.

One preferred embodiment falls under the definition of Formula Ia:

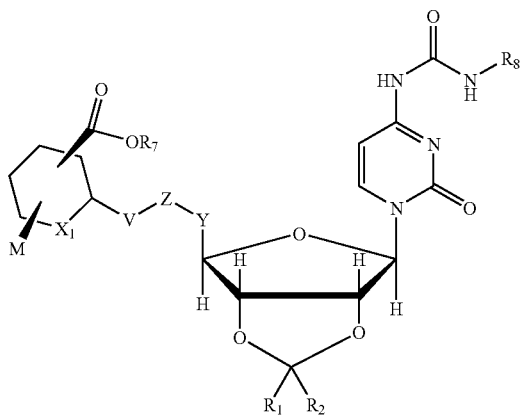

wherein:
the ring incorporating $X_1$ is taken to mean a saturated or unsaturated ring;
$R_1$ is aryl or aralkyl (e.g. phenyl, benzyl, or styryl);
$R_2$ is H;
Z is O, CH$_2$, or NH;
V is CH$_2$, NH, O, SO$_2$, or C═O;
Y is CH$_2$, or C═O;

with the proviso that V or Y are not both C═O; and
if V═O, Z is not NH;
$X_1$ is CH, C—F, C—Cl, C—Br, C—OCH$_3$, C—COOH, C—COOR$_7$ or N
M and R$_7$ are as previously defined for Formula II; and
R$_8$ is alkyl, cycloalkyl, alkylcycloalkyl, or aryl.
Preferred structures falling under the definition of Formula Ia include:
2',3'-trans-cinnamylacetal-5'-(2-carboxy)benzyloxy-6-N-ethylurea cytidine (1); 2',3'-trans-cinnamylacetal-5'-(2-carboxy-6-fluoro)benzyloxy-6-N-ethylurea cytidine (2); 2',3'-trans-cinnamylacetal-5'-(2-carboxy-6-chloro)benzyloxy-6-N-ethylurea cytidine (3); 2',3'-trans-cinnamylacetal-5'-[2-(3-carboxy)pyridylmethyloxy]-6-N-ethylurea cytidine (4); 2',3'-trans-phenylacetal-5'-(2-carboxy)benzyloxy-6-N-ethylurea cytidine (5); 2',3'-trans-phenylacetal-5'-(2-carboxy-6-fluoro)benzyloxy-6-N-ethylurea cytidine (6); 2',3'-trans-phenylacetal-5'-(2-carboxy-6-fluoro)benzoylanino-6-N-ethylurea cytidine (7); 2',3'-trans-phenylacetal-5'-[(2-carboxy)benzylamino]carbonyl-6-N-ethylurea cytidine (8); 2',3'-trans-phenylacetal-5'-[2-(3-carboxy)pyridylmethyloxy]-6-N-ethylurea cytidine (9); 2',3'-trans-phenylacetal-5'-[2-(3-carboxy)pyridylmethyloxy]-6-N-cyclopropylurea cytidine (10); 2',3'-trans-phenylacetal-5'-(2-carboxy)benzyloxy-6-N-cyclopropylurea cytidine (11); 2',3'-trans-phenylacetal-5'-(2-carboxy-6-fluoro)benzyloxy-6-N-cyclopropylurea cytidine (12); 2',3'-trans-cinnamylacetal-5'-(2-carboxy)cyclohexylmethyloxy-6-N-ethylurea cytidine (13); 2',3'-trans-phenylacetal-5'-(2-carboxy)cyclohexylmethyloxy-6-N-ethylurea cytidine (14); and 2',3'-trans-phenylacetal-5'-(2-carboxy)cyclohexylmethyloxy-6-N-cyclopropylurea cytidine (15).

A second preferred embodiment falls under the definition of Formula Ib:

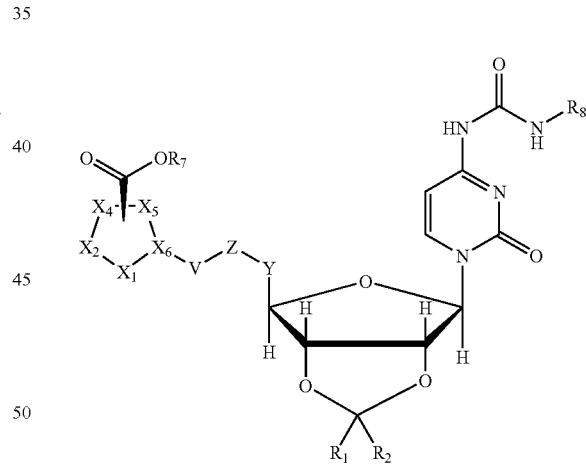

wherein
$R_1$, $R_2$, $R_7$, and $R_8$ are as defined in formula Ia;
$X_1$, $X_2$, $X_4$, $X_5$, and $X_6$ are taken to mean a ring with or without unsaturation and are independently selected from the group consisting of: N, C, S, or O; and
$X_1$-$X_6$ are taken to mean a ring of from three to five atoms;
V is NH, CH$_2$, or C═O;
Y is CH$_2$ or C═O; and
Z is O, CH$_2$, NH, S or SO$_2$.
Preferred structures falling under the definition of Formula Ib include:
2',3'-trans-cinnamylacetal-5'-[2-(3-carboxy)furanylmethyloxy]-6-N-ethylurea cytidine (16); 2',3'-trans-cinnamylacetal-5'-[2-(3-carboxy)thiophenenylmethyloxy]-6-N-ethylurea cytidine (17); 2',3'-trans-cinnamylacetal-5'-[2-(3-carboxy)furanylmethyloxy]-6-N-cyclopropylurea cytidine (18); 2',3'-trans-cinnamylacetal-5'-(2-carboxy)cyclopentyl-methytoxy-6-N-ethylurea cytidine (19); 2',3'-trans-cinnamy-lacetal-5'-(2-carboxy)cyclopentylmethyloxy-6-N-cyclopropylurea cytidine (20); 2',3'-trans-phenylacetal-5'-[2-(3-carboxy)furanylmethyloxy]-6-N-ethylurea cytidine (21); 2',3'-trans-phenylacetal-5'-[2-(3-carboxy)thiophenenylm-ethyloxy]-6-N-cyclopropylurea cytidine (22); 2',3'-trans-phenylacetal-5'-[2-(3-carboxy)thiophenenylmethyloxy]-6-N-ethylurea cytidine (23); 2',3'-trans-phenylacetal-5'-(2-carboxy)cyclopentylmethyloxy-6-N-ethylurea cytidine (24); 2',3'-trans-phenylacetal-5'-(2-carboxy)cyclopentylmethy-loxy-6-N-cyclopropylurea cytidine (25); 2',3'-trans-pheny-lacetal-5'-(2-carboxy)cyclopropylmethyloxy-6-N-ethylurea cytidine (26); and 2',3'-trans-cinnamylacetal-5'-(2-carboxy)cyclopropylmethyloxy-6-N-ethylurea cytidine (27).

A third preferred embodiment falls under the definition of Formula Ic:

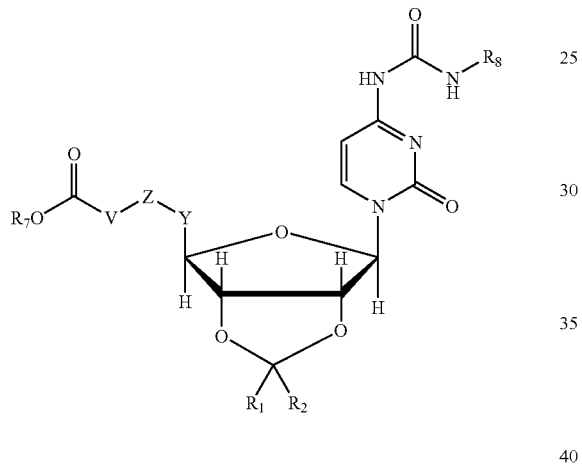

wherein:
R$_1$, R$_2$, R$_7$, and R$_8$ are as defined in formula Ia;
V is CH$_2$, NH, or O;
Z is O, CH$_2$, C=O, NH, S, SO, or SO$_2$; or
V and Z are absent; and
Y is CH$_2$, or C=O.
with the proviso that both Z and Y are not C=O.

Preferred structures falling under the definition of Formula Ic include:
2',3'-trans-cinnamylacetal-5'-(2-carboxy)methyleno-6-N-ethylurea cytidine (28); 2',3'-trans-cinnamylacetal-5'-(2-car-boxy)methyloxy-6-N-ethylurea cytidine (29); 2',3'-trans-cin-namylacetal-5'-(2-carboxy)methylamino-6-N-ethylurea cytidine (30); 2',3'-trans-phenylacetal-5'-(2-carboxy)methyl-eno-6-N-ethylurea cytidine (31); 2',3'-trans-phenylacetal-5'-(2-carboxy)methyloxy-6-N-ethylurea cytidine (32); and 2',3'-trans-phenylacetal-5'-(2-carboxy)methylamino-6-N-ethylurea cytidine (33).

Novel Compounds

The present invention provides novel compounds of Formulas I, Ia, Ib, and Ic, as listed above. Exemplary compounds of the present invention falling under the definition of Formula Ia are:

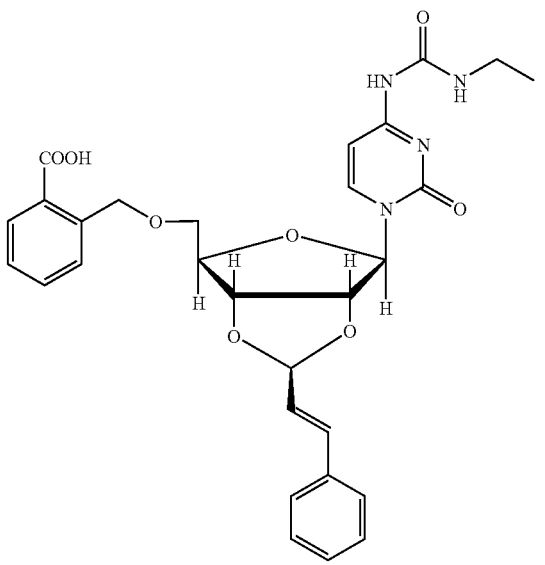

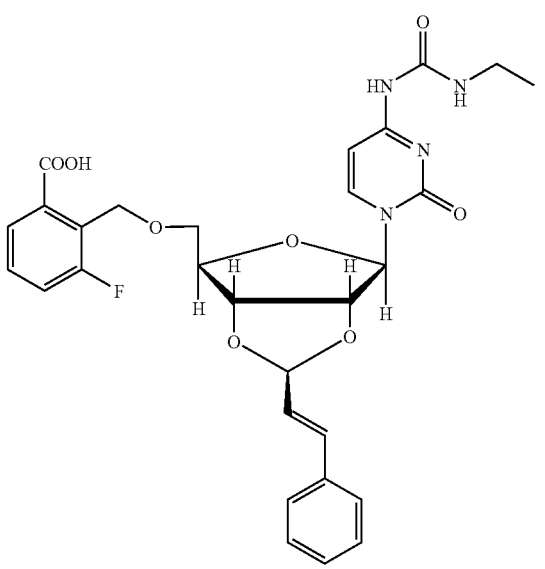

3
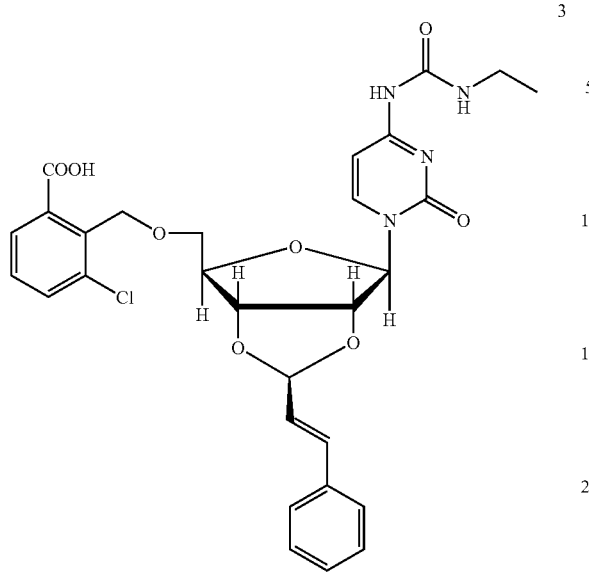
4
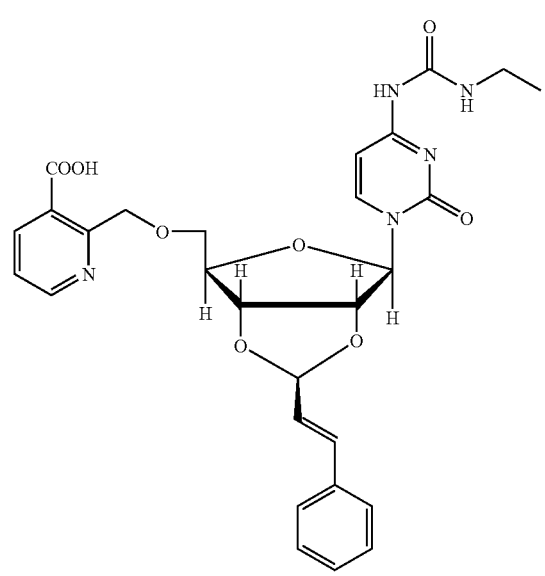
5
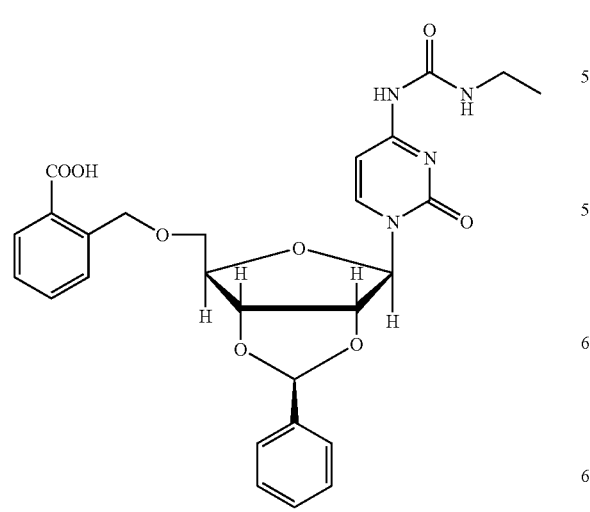
6
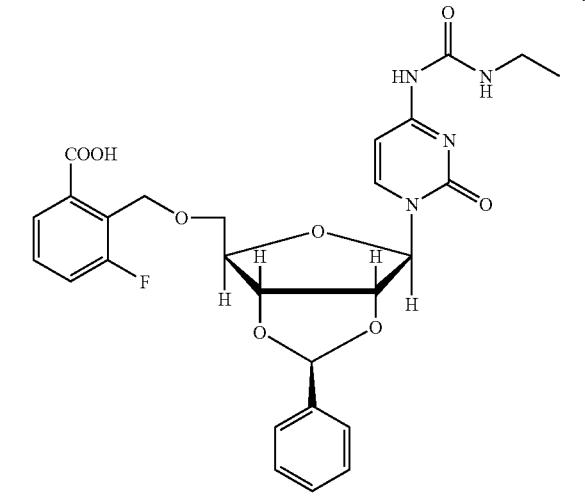
7
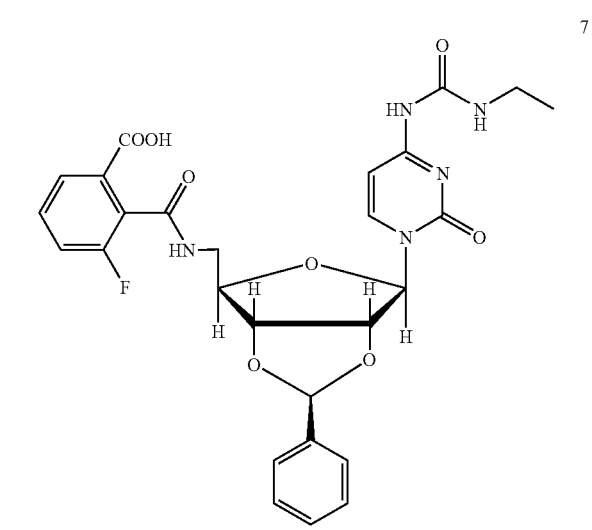
8
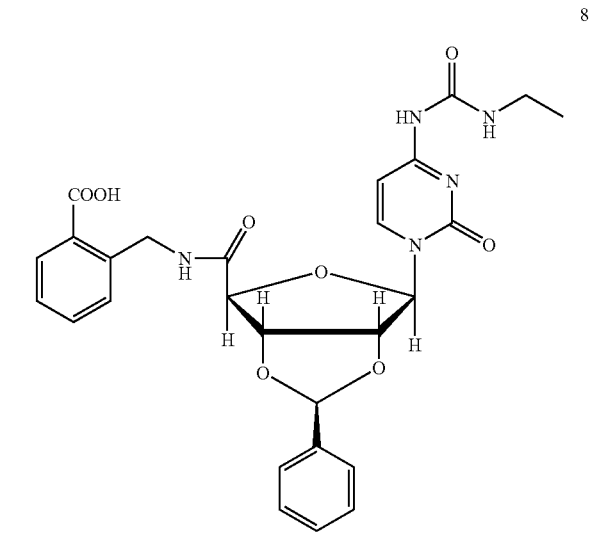

15
-continued
9
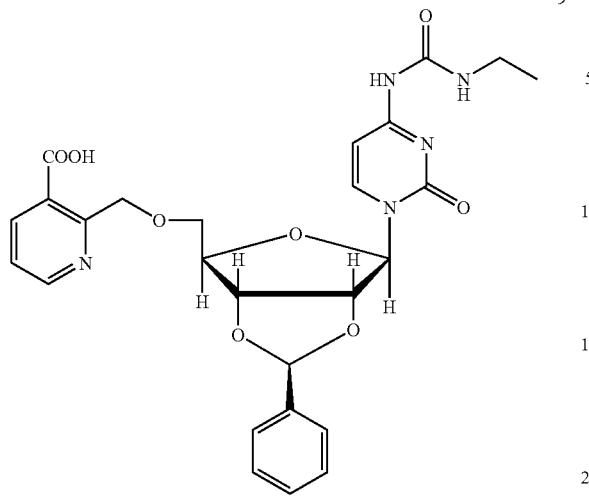
10
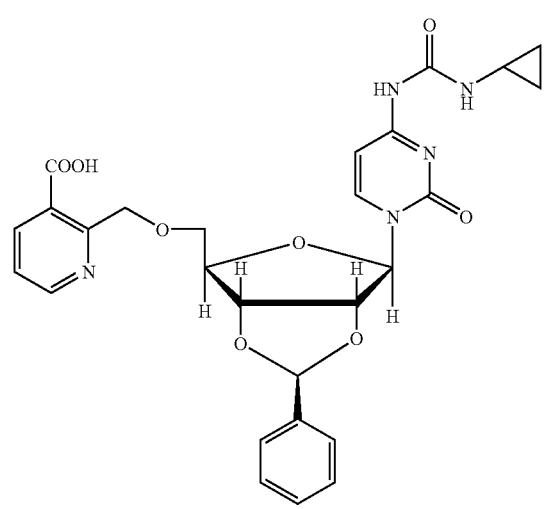
11
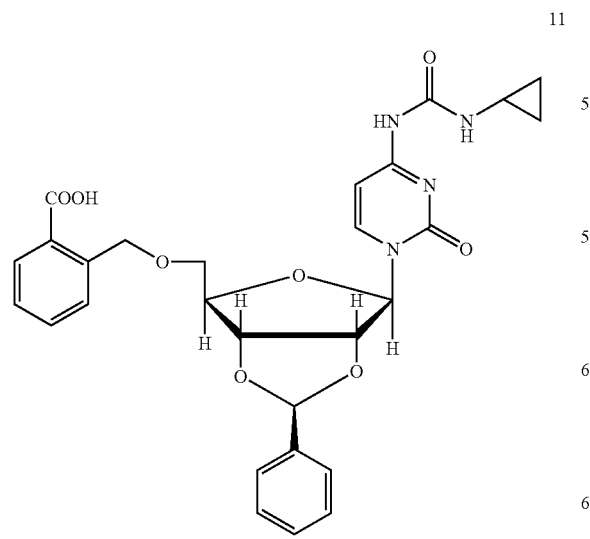
16
-continued
12
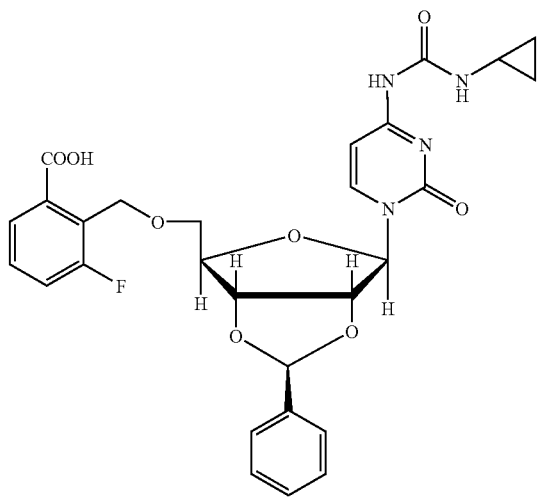
13
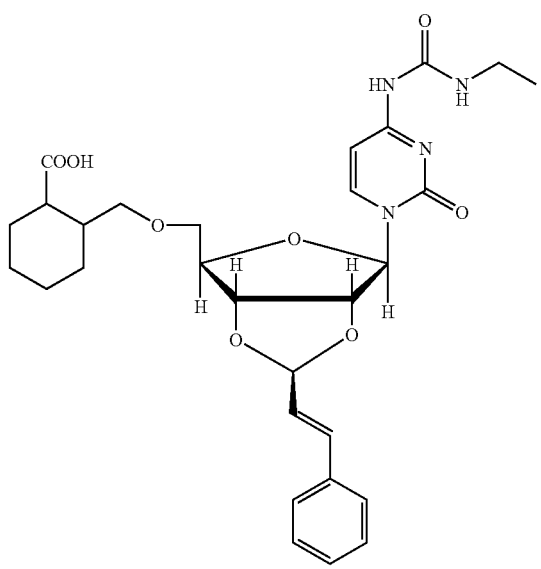
14
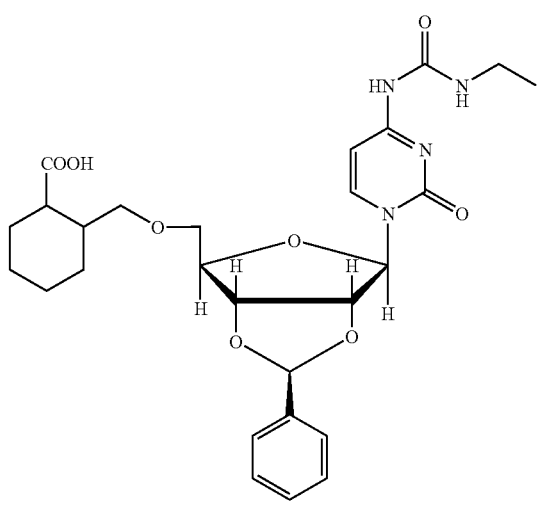

15
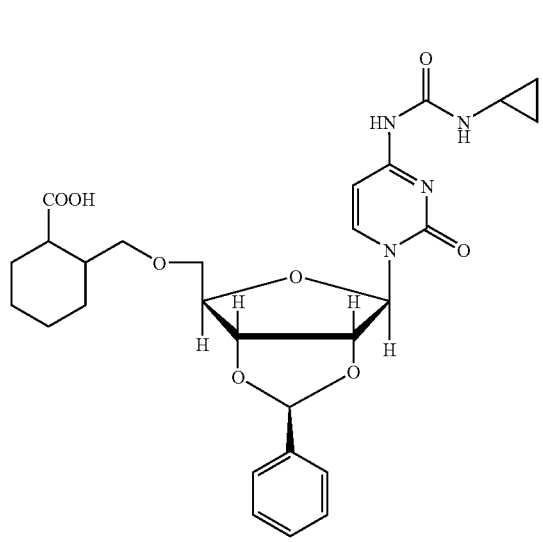
16
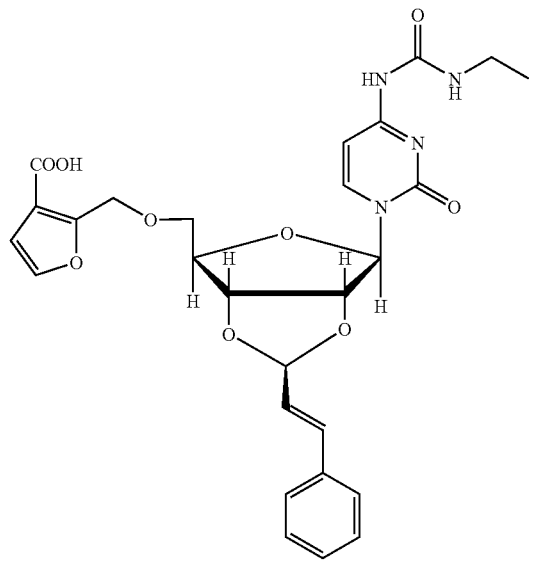
17
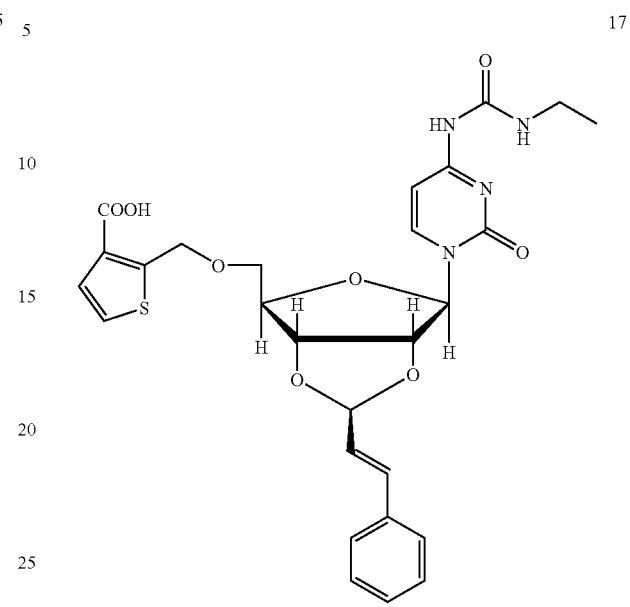
18
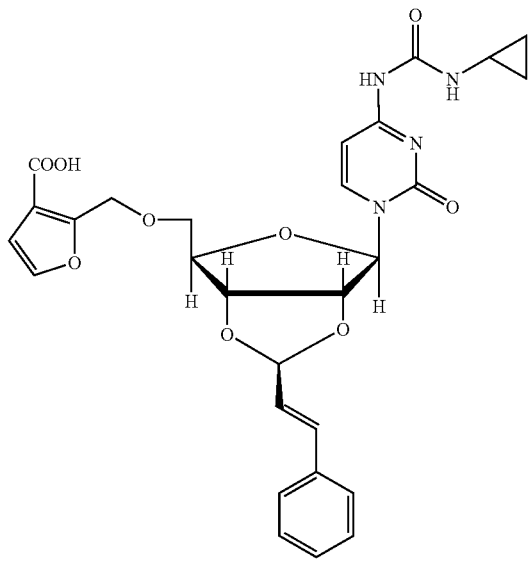
Exemplary compounds of the present invention falling under the definition of Formula Ib are:

19
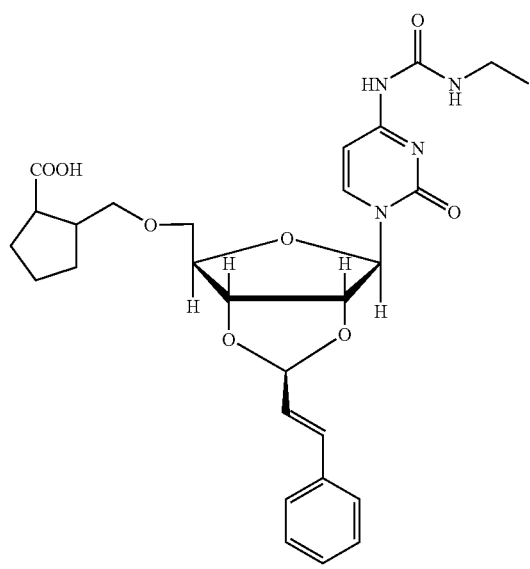
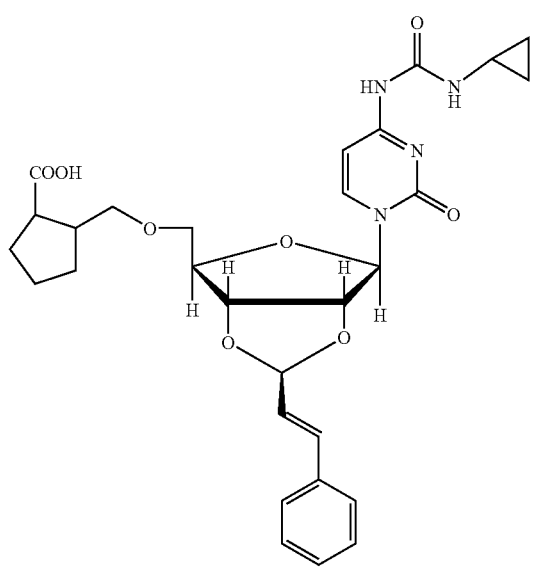
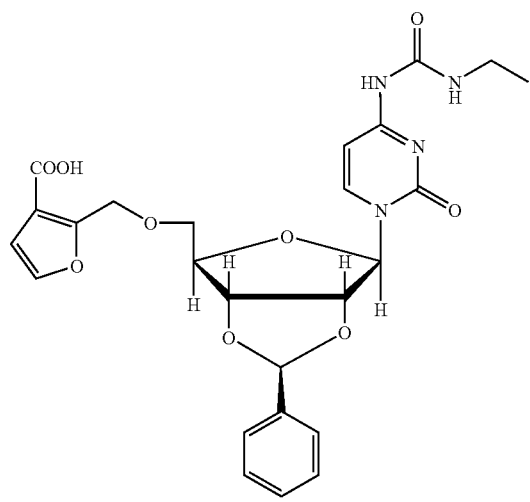
20
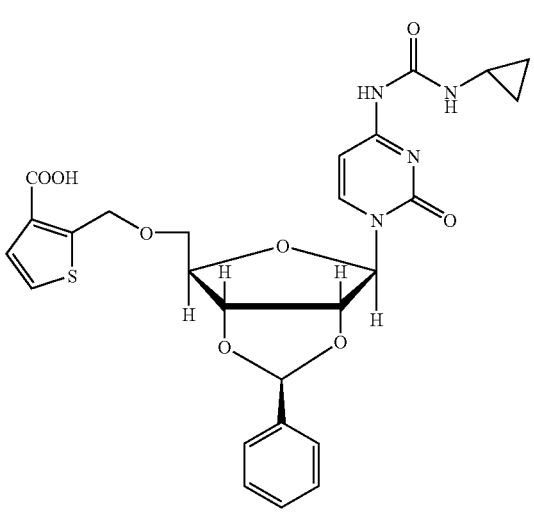
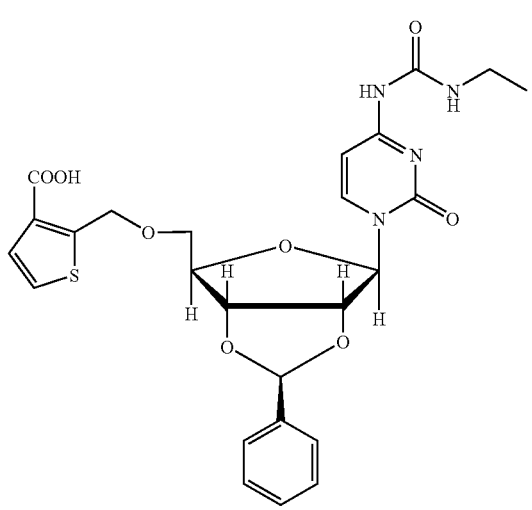
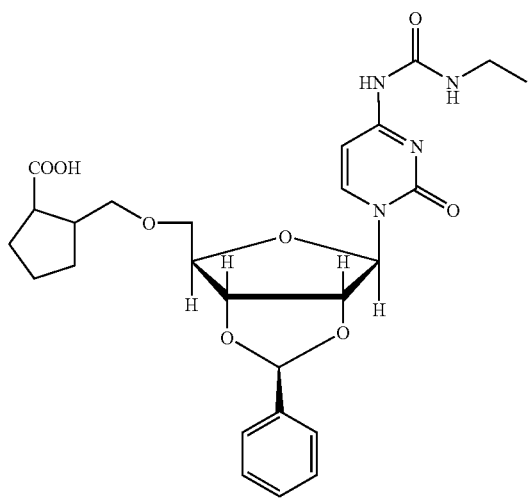

Exemplary compounds of the present invention falling under the definition of Formula Ic are:
25
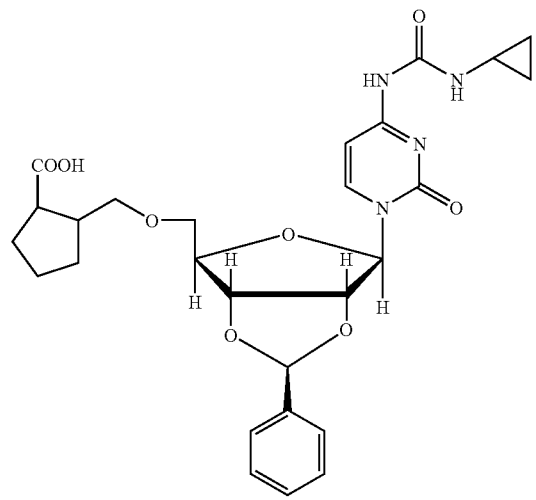
26
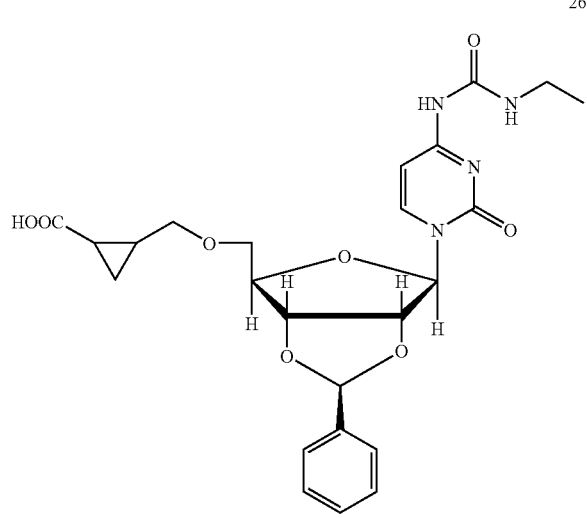
27
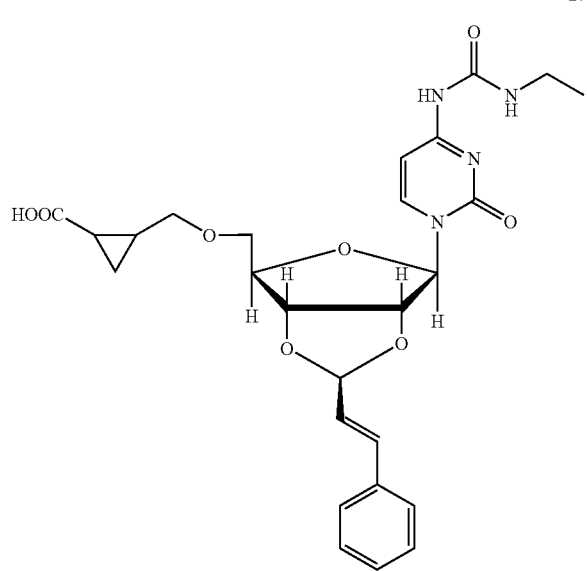
28
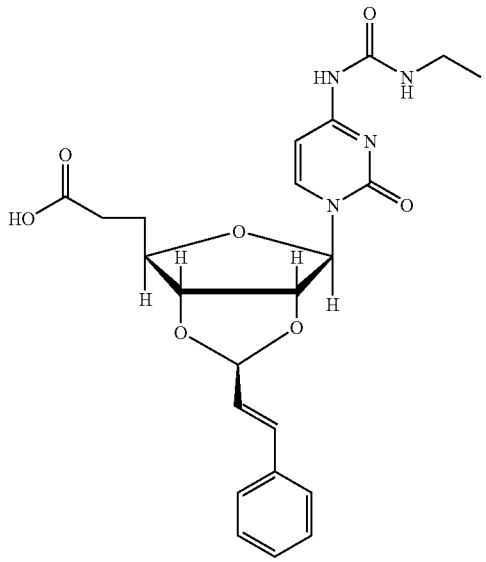
29
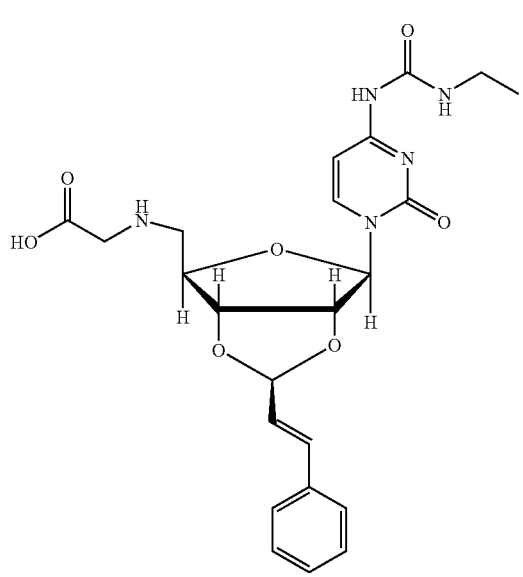

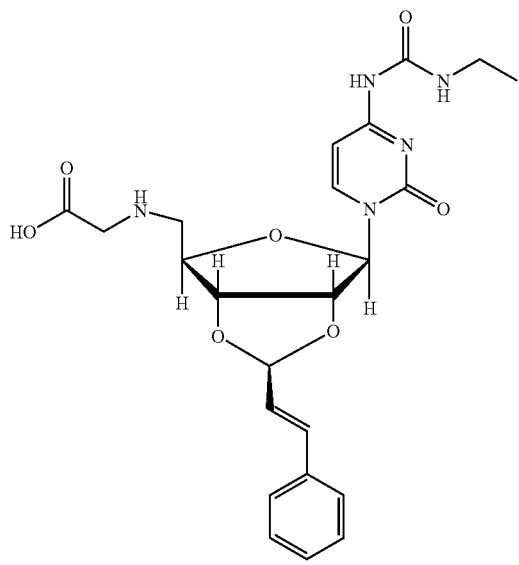

30

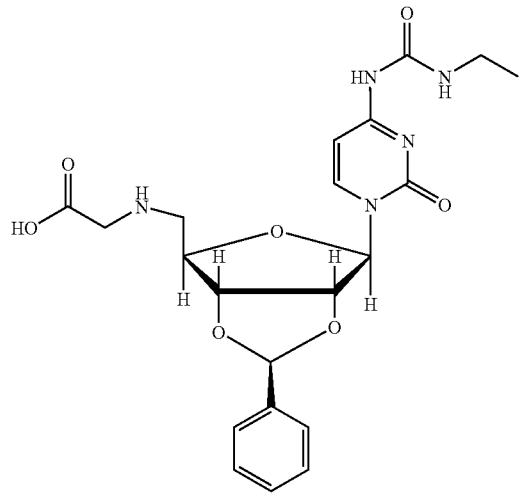

33

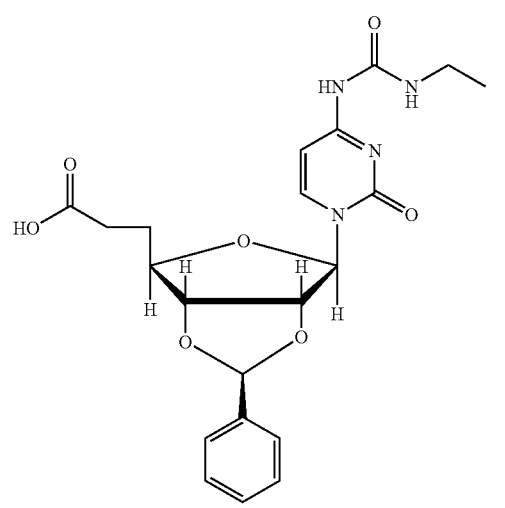

31

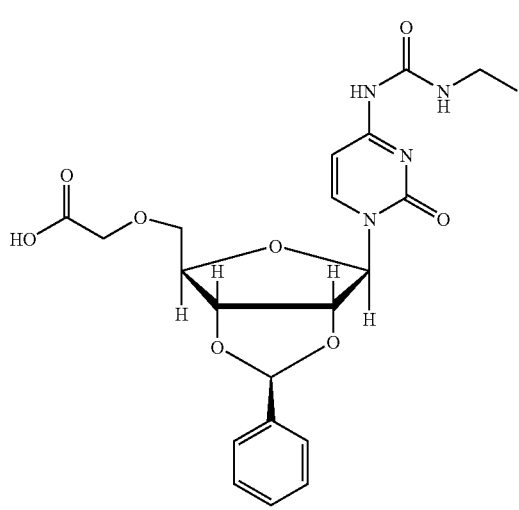

32

Pharmaceutical Formulations

The present invention additionally provides novel pharmaceutical formulations comprising compounds of Formula I, Ia, Ib, or Ic and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicy modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation of the present invention provides an aqueous solution comprising water, suitable ionic or non-ionic tonicity modifiers, suitable buffering agents, and a compound of Formula I, Ia, Ib, or Ic. In one embodiment, the compound is at 0.005 to 3% w/v, and the aqueous solution has a tonicity of 200-400 mOsm/kG and a pH of 4-9.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to intravenous administration.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 3.5-5%, and more preferably 4.2-5% w/v.

Those skilled in the art will recognize various synthetic methodologies which may be employed to prepare non-toxic pharmaceutically acceptable salts and prodrugs of the compounds.

Preparation of the Compounds

The compounds of the present invention may be synthesized by those skilled in the art using conventional synthesis methodology and well-known workup and purification procedures. The following list of references, along with references cited therein, disclose general procedures employed for the synthesis of a number of intermediates and compounds related to the present invention: Baraldi, et al., *Journal of Medicinal Chemistry*, 39(3): 802-806 (1996); Camaioni, et al., *Bioorganic & Medicinal Chemistry*, 5(12): 2267-2275 (1997); Zablocki, et al, PCT International Publication No. WO01/40243; Zablocki, et al, PCT International Publication No. WO01/40246; Mantell, et al., PCT International Publication No. WOOI/94368; Jacobson, et al., *Journal of Medicinal Chemistry*, 38(10): 1720-1735 (1995); Cristalli, et al., *Journal of Medicinal Chemistry*, 38(9): 1462-1472 (1995); Secrist, III and Talekar, *Nucleosides & Nucleotides*, 9(4): 619-27 (1990); Secrist, III, U.S. Pat. No. 4,794,174 (1988); Lyga and Secrist, III, *Journal of Organic Chemistry*, 48(12): 1982-1988 (1983); Dixon, et al., PCT International Publication No. WO02/096248; Hardern, et al., PCT International Publication No. WO01/36438; Guile et al., PCT International Publication No. WO00/04021; Lee, et al., *Bioorganic & Medicinal Chemistry Letters*, 13(6): 1087-1092 (2003); Cox, et. al., U.S. Pat. No. 5,747,496 (1998).

In many cases, commercially available starting materials can be used for the synthesis of compounds of this invention. When not available commercially, useful starting materials can either be obtained from stepwise modification of commercially-available compounds and derivatives, or they may be synthesized from simpler precursors using literature methods known in the art. Other appropriate intermediates can be purchased from commercial sources and used as starting materials for compounds of the present invention, or can be synthesized as described in the chemical literature.

Those having skill in the art will recognize that the starting materials can be varied and additional steps employed to produce compounds encompassed by the present invention, as shown in the above schemes and as demonstrated by the examples which follow. In some cases, protection of certain reactive functionalities may be necessary to achieve some of the above transformations. In general, the need for such protecting groups as well as the conditions necessary to attach and remove such groups will be apparent to those skilled in the art.

Scheme 1. Preparation of 5'-modified ethers by nucleophilic aromatic substitution.

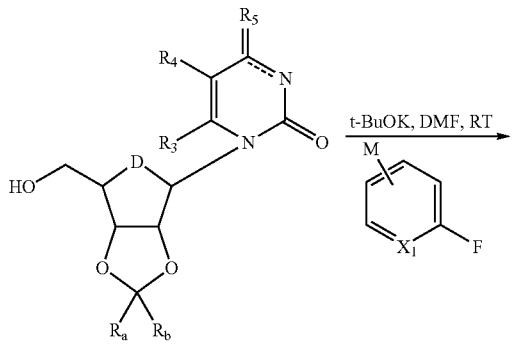

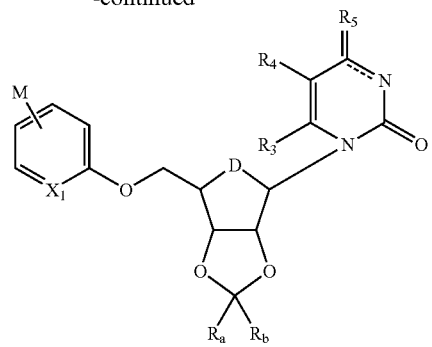

Scheme 1, for example, discloses a useful method for the synthesis of 5'-aryl- or 5'-heteroaryl-ether derivatives by substitution of an appropriately functionalized cytidine analogue for a halogen on an appropriately-substituted halogenated aromatic compound or a related heteroaromatic derivative. Groups not defined in Scheme 1 are defined as in Formula I. Preferred substituents at M of the aromatic-/heteroaromatic-group in Scheme 1 are hydrogen, or halogen, or groups containing carboxylic acid derivatives such as: —$CO_2R_3$; but they can also be halogen, or esters or amides of alkylcarboxylic acids, arylcarboxylic acids, —O-(alkylcarboxylic acids), —NR-(alkylcarboxylic acids), and the like. When M is halogen in Scheme 1, preferred halogens are chloro and fluoro.

Scheme 2. Preparation of 5'-modified ethers by Mitsunobu coupling of phenols.

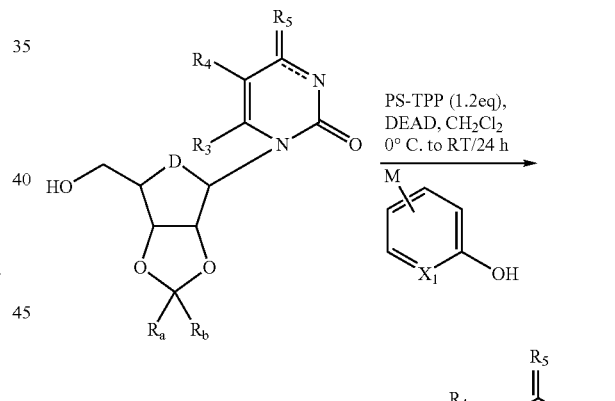

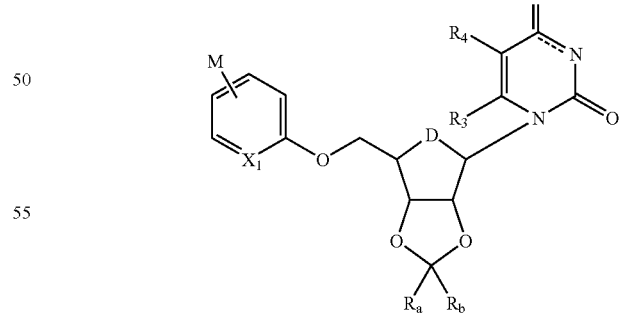

5'-Substituted aryl derivatives can also be prepared via Mitsunobu coupling of phenols (Mitsunobu, *Synthesis* 1-28 (1981); Brown, et al., *J. Med. Chem.* 37 (5), 674-88 (1994); Santosh and Balasubramanian, *Synthetic Communications*, 24(8), 1049-62 (1994)) to derivatives of cytidine as provided in Scheme 2. Groups in Scheme 2 are defined as in Formula I. Some preferred substituents at M of the aromatic/heteroaromatic-group in Scheme 2 independently can be hydrogen, halogen, alkyl, alkoxy, aryl or groups containing carboxylic acid derivatives such as: —$CO_2R_3$; but esters or amides of alkylcarboxylic acids, arylcarboxylic acids, —O-(alkylcarboxylic acids), —NR-(alkylcarboxylic acids), and the like are also included. When M is halogen in Scheme 2, preferred halogens are chloro and fluoro.

Use of $P2Y_{12}$ Receptor Antagonist Compounds

This invention provides a method of preventing or treating diseases or conditions associated with platelet aggregation and/or platelet activation. This invention also provides a method for solving treatment problems or limited treatment options caused by the aggregation of platelets or by the irreversible inhibition of platelet aggregation.

This invention provides methods of preventing or treating thrombosis and related disorders, such as venous thrombosis, established peripheral arterial disease, thrombophlebitis, arterial embolism, coronary and cerebral arterial thrombosis, unstable angina, myocardial infarction, stroke, cerebral embolism, renal embolism, pulmonary embolism and other embolism- or thrombosis-related afflictions produced by but not limited to procedural or surgical interventions. This invention further provides methods for the prevention of embolism or thrombosis during percutaneous coronary interventions, placement of coronary stents, coronary angioplasty, coronary endarectomy, carotid endarterectomy, or due to platelet-aggregation complications related to atherosclerosis, inflammation, exposure of blood to artificial devices, drug effects.

This invention further provides methods of inhibiting platelet aggregation in blood and blood products comprising platelets, such as stored blood.

The method comprises administering to a subject or blood and blood products a composition comprising an effective amount of $P2T_{12}$ receptor antagonist compound, wherein said amount is effective to bind the $P2Y_{12}$ receptors on platelets and inhibit platelet aggregation, preferably in a reversible manner.

The invention further provides useful methods of treating patients to inhibit platelet aggregation in a reversible manner, especially in patients that are subject to a procedure such as percutaneous coronary interventions, stent placement, balloon angioplasty, coronary atherectomy, coronary endarterectomy, carotid endarterectomy, thrombolytic theraphy, coronary or other vascular graft surgery, dialysis, etc. In those patients, it is important that platelet aggregation inhibition can be rapidly reversed (within hours for oral administration and within minutes for intravenous administration) if necessary. The method comprises the steps of: (a) providing a patient in need of rapid reversal of platelet aggregation inhibition; (b) administering a therapeutically effective amount of a compound of Formula I, Ia, or Ic to the patient; (c) submitting the patient to a procedure selected from the group consisting of: percutaneous coronary interventions, stent placement, balloon angioplasty, coronary atherectomy, coronary endarterectomy, carotid endarterectomy, thrombolytic theraphy, coronary or other vascular graft surgery, and dialysis, (d) discontinuing the administering of said compound to the patient; and (e) allowing the amount of said compound in the patient's blood to reduce to below an therapeutically effective amount. In step (b), the administration of the compound can be either continuous or intermittent as long as it provides a therapeutically effective amount of the compound in the patient's blood. The amount of the compound in the patient's blood is monitored.

The compounds of general Formulae I, Ia-Ic are antagonists of the effect of ADP on its platelet membrane receptor, the $P2Y_{12}$ receptor. The compounds of general Formula I are useful in therapy, in particular in the prevention or treatment of platelet aggregation. The compounds provide efficacy as antithrombotic agents by their ability to block ADP from acting at its platelet receptor site and thus prevent platelet aggregation. The compounds provide a more efficacious antithrombotic effect than aspirin, but with less profound effects on bleeding than antagonists of the fibrinogen receptor.

The $P2Y_{12}$ receptor antagonists of this invention, in contrast with currently available marketed products clopidogrel (Plavix®) and ticlopidine (Ticlid®), bind to the $P2Y_{12}$ receptor in a reversible fashion and therefore, the effects of the treatment with compounds described in this invention are reversed by the simple discontinuation of the treatment, restoring the hemostatic functionality of the platelet as necessary. Since platelets are non-nucleated cell particles that lack the ability to synthesize new proteins, treatment of subjects with irreversible $P2Y_{12}$ antagonists results in the impairment of platelet finction that lasts for the lifespan of the platelet (approximately 8 to 10 days). The use of irreversible $P2Y_{12}$ antagonists such as clopidogrel has been associated with increases in blood loss, transfusion requirements and rate of reoperation after cardiac surgery (Kapetanakis, et al., *Eur Heart J.* 26: 576-83, 2005). To avoid these complications, subjects undergoing elective surgeries are required to discontinue the treatment with irreversible antagonists for at least five days prior to the surgery, which increases the risk of a thrombotic event during this period. Therefore, the compounds described in this invention represent an advantage over the currently marketed compounds.

The ADP-induced platelet aggregation is mediated by the simultaneous activation of both $P2Y_{12}$ and $P2Y_1$ receptors, thus the combined administration of the Formula I compounds with antagonists of platelet $P2Y_1$ receptors can provide a more efficacious antithrombotic effect at concentrations of each antagonist that are below the effective concentrations to block each receptor subtype in other systems, resulting in a decrease of the potential manifestation of adverse effects. In addition, these compounds can be used in conjunction with lower doses of other platelet aggregation inhibitors, which work by different mechanisms, to reduce the possible side effects of said agents.

The compounds of the present invention are useful as antithrombotic agents, and are thus useful in the treatment or prevention of unstable angina, coronary angioplasty (PTCA) and myocardial infarction.

The compounds of the present invention are useful in the treatment or prevention of primary arterial thrombotic complications of atherosclerosis such as thrombotic stroke, peripheral vascular disease, and myocardial infarction without thrombolysis.

The compounds of the invention are usefuil for the treatment or prevention of arterial thrombotic complications due to interventions in atherosclerotic disease such as angioplasty, endarterectomy, stent placement, coronary and other vascular graft surgery.

The compounds of the invention are useful for the treatment or prevention of thrombotic complications of surgical or mechanical damage such as tissue salvage following surgical or accidental trauma, reconstructive surgery including skin flaps, and "reductive" surgery such as breast reduction.

The compounds of the present invention are useful for the prevention of mechanically-induced platelet activation in vivo, for example, caused by cardiopulmonary bypass, which results in temporary platelet dysfunction (prevention of microthromboembolism). The compounds of the present invention are useful for prevention of mechanically-induced platelet activation in vitro. For example, the compounds are useful in the preservation of blood products, e.g. platelet concentrates, prevention of shunt occlusion such as renal dialysis and plasmapheresis, and thrombosis secondary to vascular damage/inflammation such as vasculitis, arteritis, glomerulonephritis and organ graft rejection.

The compounds of the present invention are useful in disorders with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

The compounds of the invention are useful for the treatment or prevention of venous thrombosis such as deep vein thrombosis, veno-occlusive disease, hematological conditions such as thrombocythemia and polycythemia, and migraine.

The compounds of the present invention are useful in treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The compounds of the present invention are useful in treating chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TrP), snake venom and immune diseases, are likely to be responsive to such treatment.

The compounds of the present invention are useful in treating diseases or conditions associated with platelet activation and/or aggregation produced by the contact of blood with an artificial device. In one embodiment, the artificial device is a paracorporeal artificial lung and an extracorporeal membrane oxigenation device. In another embodiment, the artificial device is an internal implantable artificial heart. In another embodiment, the artificial device is an apheresis instrument used to remove or isolate a specific component of the blood, and returning the remaining blood components to the donor. In yet another embodiment, the artificial device is a hemodialysis instrument.

The compounds of the present invention are useful in vitro to inhibit the aggregation of platelets in blood and blood products, e.g. for storage, or for ex vivo manipulations such as in diagnostic or research use. In such applications, the compounds are administered to the blood or blood product.

Finally, if the compounds of the present invention have sufficient binding affinity and bear a fluorescent moiety, they are useful as biochemical probes for the $P2Y_{12}$ receptor.

In a preferred embodiment, the compounds are used in the treatment of unstable angina, coronary angioplasty and myocardial infarction.

In another preferred embodiment, the compounds are useful as adjunctive therapy in the prevention or treatment of thrombotic disorders, such as coronary arterial thrombosis during the management of unstable angina, coronary angioplasty and acute myocardial infarction, i.e. perithrombolysis. The compounds are administered in combination with other antiplatelet and/or anticoagulant drugs such as heparin, aspirin, GP IIb/IIIa antagonists, or thrombin inhibitors.

This invention provides a method of inhibiting platelet aggregation and clot formation in a mammal, especially a human, which comprises administering to the subject a compound of Formula (I) and a pharmaceutically acceptable carrier.

This invention further provides a method for inhibiting the reocclusion of an artery or vein following fibrinolytic therapy, which comprises administering to a subject a compound of Formula (I) and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention can be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The active compounds can be administered systemically to target sites in a subject in need such that the extracellular concentration of a $P2Y_{12}$ antagonist is elevated to block the binding of ADP to $P2Y_{12}$ receptor, thus inhibit the platelet aggregation. The term systemic as used herein includes subcutaneous injection, intravenous, intramuscular, intrastemal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile injectable preparation can be a sterile injectable solution or suspension in a non-toxic acceptable diligent or solvent. Among the acceptable vehicles and solvents that can be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds can also be systemically administered to the platelet aggregation sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target platelets in a pharmaceutically effective amount. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Intravitreal delivery can include single or multiple intravitreal injections, or via an implantable intravitreal device that releases $P2Y_{12}$ antagonists in a sustained capacity. Intravitreal delivery can also include delivery during surgical manipulations as either an adjunct to the intraocular irrigation solution or applied directly to the vitreous during the surgical procedure.

For systemic administration, plasma concentrations of active compounds delivered can vary according to compounds; but are generally $1 \times 10^{-10}$-$1 \times 10^{-4}$ moles/liter, and preferably $1 \times 10^{-8}$-$1 \times 10^{-5}$ moles/liter.

The pharmaceutical utility of $P2Y_{12}$ antagonist compounds of this invention is indicated by their inhibition of ADP-induced platelet aggregation. This widely used assay, as described in S. M. O. Hourani et al. *Br. J. Pharmacol.* 105, 453-457 (1992) relies on the measurement of the aggregation of a platelet suspension upon the addition of an aggregating agent such as ADP.

The invention is illustrated further by the following examples that are not to be construed as limiting the invention in scope to the specific procedures described in them.

EXAMPLES

Example 1

Synthesis of Compounds a. 2',3'-cinnamylacetal cytidine

Cytidine (10.0 g, 41.1 mmol) was suspended in trans-cinnamaldehyde (36 mL, 290 mmol) and the mixture cooled below −10° C. Trifluoroacetic acid (33.2 mL, 432 mmol) was added and the mixture stirred for 3.5 hrs at which point the reaction was done as determined by high performance liquid chromatography (HPLC). The reaction mixture was diluted with isopropyl acetate (135 mL) and the acid neutralized by the addition of 5N sodium hydroxide. This led to the precipitation of the title compound, which was separated from the liquid phase by decantation, followed by filtration. The solid was washed with water and dried to a powder. (5.38 g, 37% yield)

b. 2',3'-(trans) cinnamylacetal cytidine

2',3'-cinnamylacetal cytidine (1.0 g, 2.8 mmol) was mixed with tetrahydrofuran (5.4 mL) and water (1.3 mL) and the slurry warmed to 40° C. At this temperature, p-toluenesulfonic acid monohydrate (0.532 g, 2.8 mmol) was added and the reaction mixture was heated overnight. The next day, a small amount of the undesired cis isomer was still evident by HPLC, so a further portion of the acid (130 mg) was added and the reaction continued for an additional 15 minutes. The reaction solution was diluted with isopropyl acetate (15 mL), and the acid neutralized with 0.5 N sodium hydroxide. This led to a white precipitate being formed in the isopropyl acetate layer, which was filtered off and washed with isopropyl acetate. Drying gave the title compound (0.442 mg, 44%). This single trans isomer had much better chemical stability relative to the corresponding cis acetal isomer, making it much more desireable from a pharmaceutical perspective. As such, it could be used to prepare the preferred compounds of the present invention which contain a cinnamyl acetal moiety.

c. 2',3'-cinnamylacetal-5'-TBS cytidine

2',3'-cinnamylacetal cytidine (2.20 g, 6.16 mmol)) was dissolved in N,N-dimethylformamide (15 mL) and imidazole (1.26 g, 18.5 mmol) added. T-butyldimethylsilyl chloride (1.86 g, 12.3 mmol) was added and the mixture heated for 6 hours at 50° C. The mixture was diluted with dichloromethane(40 mL) and washed with 50% saturated sodium chloride (3×20 mL). The dichloromethane layer was dried over magnesium sulfate andhe solvent was removed. The product (2.80 g) used without further purification in the next reaction.

d. 2',3'-cinnamylacetal-5'-TBS-6-N-ethylurea cytidine

2',3'-cinnamylacetal-5'-TBS cytidine from the previous reaction (1.0 g, 2.12 mmol) was suspended in toluene (15 mL) and ethylisocyanate (0.833 mL, 10.6 mmol) and triethylamine (2.33 mmol) added. The reaction mixture was heated in a sealed bomb at 60° C. for 15 hours, after which the volatiles were removed. The yield of the title compound was 1.05 g (91%).

e. 2',3'-cinnamylacetal-6-N-ethylurea cytidine

2',3'-cinnamylacetal-5'-TBS-6-N-ethylurea cytidine (1 g, 1.84 mmol) was dissolved in tetrahydrofuran (10 mL). Tetra-n-butylammonium fluoride (2.0 mL of a 1 M solution in tetrahydrofuran; 2 mmol) added. The mixture was stirred at room temperature for two hours, after which the reaction was diluted with ethyl acetate (25 mL) and water (20 mL). The layers were separated and the organic layer was dried over sodium sulfate. The product (0.465 g, 59% yield) was used without further purification in the next reaction.

f. 2',3'-cinnamylacetal-5'-(2-carboxy-6-fluoro)benzyl-6-N-ethylurea cytidine 2',3'-cinnamylacetal-6-N-ethylurea cytidine (0.050 g, 0.12 mmol) was dissolved in N,N-dimethyl formamide (1.0 mL). Sodium hydride (60%, 0.028 g, 0.70 mmol) was added and the orange solution stirred for 5 min. To this solution was added (2-carboxymethyl-6-fluoro) benzyl bromide (0.029 mL, 0.163 mmol) and the reaction stirred at room temperature for 1 hr. During the course of this alkylation, the ester was hydrolyzed to the carboxylic acid. The mixture was quenched with acetic acid and the product isolated via preparative HPLC ($C_{18}$ column, gradient from 0.05 M amamonium acetate to acetonitrile) Yield of purified title compound was 0.020 g (30%).

$^1$H NMR ($CDC_3$, 300 MHz): δ 1.25 (t, 3H), 3.41 (m, 2H), 3.69 (m, 1H), 3.92 (m, 1H), 4.49 (s, 1H), 4.93 (m, 4H), 5.73 (d, 1H), 5.99 (m, 2H), 6.76 (d, 1H), 7.33 (m, 8H), 7.74 (d, 1H), 7.95 (s, 1H).

MW calculated for $C_{29}H_{29}FN_4O_8$=580.2; found 579.19 ($MH^-$)

g. 2',3'-trans-cinnamylacetal-5'-(2-carboxy-fluoro) benzyloxy-6N-ethylurea cytidine (Compound 2)

By virtue of the chosen chemistry, the product from Step f comprised a mixture of two diastereomers, i.e., cis or trans acetal. To prepare pure trans diastereomer compound 2, the mixture of products generated in Example If was treated with aqueous acid, which cleaved the unwanted cis isomer, leaving only the single trans isomer compound 2.

h. 2',3'-trans-cinnamylacetal-5'-(2-carboxy)benzyloxy-6-N-ethylurea cytidine (Compound 1)

To prepare the pure trans diastereomer of compound 1, the unwanted cis isomer generated in Example 1a was cleaved according to Example 1b, giving 2',3'-(trans) cinnamylacetal cytidine, and the remaining steps (1c-1f) were carried out using the single trans isomer. (2-carboxymethyl) benzyl bromide was used as the alkylating agent in the final step.

Example 2

Inhibition of ADP-Induced Platelet Aggregation

Isolation of platelets: Human blood is obtained from informed healthy adult volunteers. Blood is collected into one-sixth volume of acid/citrate/dextrose (ACD) buffer (85 mM sodium citrate, 65 mM citric acid, and 110 mM glucose). Collected blood is placed in a water bath at 37° C. for 30 minutes. Blood is then centrifuged at 275×g for 16 minutes at room temperature and the platelet-rich plasma is removed and centrifuged at 2200×g for 13 minutes at room temperature. The platelet pellet is resuspended in 40 mL of HEPES-buffered Tyrode's solution (137 mM NaCl, 2.7 mM KCl, 1 mM $MgCl_2$, 2 mM $CaCl_2$, 12 mM $NaHCO_3$, 0.36 mM $NaH_2PO_4$, 5.5 mM glucose, 5 mM HEPES pH 7.4, 0.35% bovine serum albumin or 0.35% human serum albumin) containing 10 U/mL heparin and 5 μM (final concentration) prostaglandin $I_2$ ($PGI_2$). The platelet suspension is incubated in a 37° C. water bath for 10 minutes and then 5 μM (final conc.) $PGI_2$ is added just before centrifugation at 1900×g for 8 minutes. The resulting pellet is resuspended in 40 mL of HEPES-buffered Tyrode's solution containing 5 μM (final concentration) $PGI_2$ and then is incubated for 10 minutes in a 37° C. water bath. A small aliquot (500 μL) of the platelet suspension is removed for platelet counting. Prior to centrifugation 5 μM (final concentration) $PGI_2$ is added to the suspension and then the suspension is centrifuged at 1900×g for 8 minutes. The pellet is resuspended at a density of 5×10$^8$ cells/mL in HEPES-buffered Tyrode's solution containing 0.05 U/mL apyrase.

Aggregation Studies: ADP-induced platelet aggregation is determined by measuring the transmission of light through a 0.5 ml suspension of stirred (1000 rpm) washed platelets in a lumi-aggregometer at 37° C. (Chrono-Log Corp. Havertown, Pa.). The baseline of the instrument is set using 0.5 ml of Hepes-buffered Tyrode's solution. Prior to aggregation measurements, the platelet suspension is supplemented with 1 mg/ml fibrinogen. Platelet aggregation is initiated by the addition of indicated concentrations of ADP or other agonists, and the light transmission is continuously recorded for at least 8 min. When inhibitors of platelet aggregation are tested, platelets are incubated for 2 min in the presence of indicated concentrations of inhibitor before addition of ADP or other agonists, and the response is recorded for at least 8 min. The potency of agonists and inhibitors of platelet aggregation is calculated from both the rate of aggregation and the maximal extent of aggregation obtained for each determination by fitting the data to a four-parameter logistic equation using the GraphPad software package (GraphPad Corp. San Diego, Calif.).

When a broad range of concentrations of $P2Y_{12}$ antagonist is tested (usually from 1 nM to 100 μM), an $IC_{50}$ value is also obtained. $IC_{50}$ values represent the concentration of antagonist necessary to inhibit by 50% the aggregation elicited by a given concentration of ADP.

Example 3

$IC_{50}$ Values Obtained from Washed Platelets

The $IC_{50}$ values for the following compounds, as inhibitors of ADP-induced aggregation of washed platelets, were determined using the procedures provided in Example 2:

2',3'-trans-cinnamylacetal-5'-(2-carboxy)benzyl-6-N-ethylurea cytidine (compound 1, tested as the single trans acetal isomer): $IC_{50}$=23.5 micromolar.

2',3'-cinnamylacetal-5'-(2-carboxy-6-fluoro)benzyl-6-N-ethylurea cytidine (tested as a mixture of cis acetal isomer and trans acetal isomer of compound 2): $IC_{50}$=1.3 micromolar.

These $IC_{50}$ values demonstrate that the compounds of the present invention which contain a pyrimidine rather than a purine core have good potency as antagonists of ADP-induced platelet aggregation.

Example 4

Inhibition of ADP-induced Platelet Aggregation in Whole Blood

Human blood is obtained from informed healthy adult volunteers. Blood is collected into syringes containing heparin, sodium citrate, PPACK or hirudin as anticoagulant. Blood is carefully transferred to a conical tube and maintained at room temperature. Assays are conducted within 60 min from the collection of the blood sample. ADP-induced platelet aggregation is performed using the impedance mode of an aggregometer (Chrono-Log Corp. Havertown, Pa.). Blood is gently mixed and an aliquot of 500 µL is transferred to a measurement cuvette, then, 450 µL of warm sterile saline is added to each cuvette and the sample is stirred at 1000 rpm. The impedance probe is introduced into the cuvette and the sample is allowed to warm for approx. 3-4 minutes in the aggregometer. The basal impedance is recorded for 1 minute and then 50 µL of the appropriate concentrations of ADP are added to generate an ADP dose response curve. For the evaluation of $P2Y_{12}$ receptor antagonists on platelet aggregation, after the basal impedance is recorded for 1 minute as indicated above, blood samples are supplemented with 50 µL of the antagonist or vehicle and after 2 minutes, 50 µL of ADP ($EC_{90}$; usually 5-10 µmol/L ADP) are added and the impedance is recorded for up to 8 minutes. The potency of agonists and inhibitors of platelet aggregation is calculated from the impedance values obtained in each sample by fitting the data to a four-parameter logistic equation using the GraphPad software package (GraphPad Corp. San Diego, Calif.).

Example 5

Effects on Platelet Aggregation In Vivo

To evaluate the ability of these compounds to inhibit platelet aggregation in vivo, an experimental protocol similar to the method of R. G. Humphries et al. (Br. J. Pharmacol. 115:1110-1116, 1995) is performed.

Surgical Preparation and Instrumentation: Male Sprague-Dawley rats are anesthetized. Body temperature is maintained at 37±0.5° C. with a heating lamp. Animals breathe spontaneously and a tracheotomy is performed to ensure a patent airway. A cannula containing heparinized saline is introduced into the left femoral artery and connected to a transducer to record blood pressure and heart rate. Cannulae containing non-heparinized saline are introduced into the left common carotid artery and left jugular vein for withdrawal of arterial blood samples and intravenous administration of compounds, respectively.

Experimental Protocol: Either compound or vehicle is administered to each animal as an infusion. Blood samples are taken immediately prior to the first infusion, at the end of each infusion and 20 min after cessation of the final infusion for measurement of platelet aggregation ex vivo. Immediately after sampling, ADP-induced platelet aggregation is measured in duplicate in 0.5 ml blood samples diluted 1:1 with saline and incubated at 37° C. for 4 min. For the final minute of this period, cuvettes are transferred to a lumi-aggregometer and the sample stirred at 900 rpm. ADP (3 µM) is added in a volume of 20 µl and the aggregation response is recorded.

Example 6

Inhibition of Thrombus Formation in Anesthetized Rats

To evaluate the effect of these compounds on thrombus formation in vivo, the following experimental protocol is performed.

Rats (CD-1; male; approximately 350 grams; Charles River, Raleigh, N.C.), are anesthetized with sodium pentobarbital (70 mg/kg i.p.). The abdomens are shaved and a 22 gauge intravenous catheter is inserted into a lateral tail vein. A midline incision is made and the intestines are wrapped in saline-soaked gauze and positioned so the abdominal aorta is accessible. The inferior vena cava and abdominal aorta are carefully isolated and a section (approximately 1 cm) of the abdominal aorta (distal to the renal arteries proximal to the bifurcation) is dissected. All branches from the aorta in this section are ligated with 4-0 silk suture. A 2.5 mm diameter flow probe connected to a Transonic flow meter is placed on the artery and a baseline (pre-stenosis) flow is recorded. Two clips are placed around the artery decreasing the vessel diameter by approximately 80%. A second baseline flow measurement is taken (post-stenosis) and the hyperemic response is tested. Animals are then treated with either compound or saline intravenously via tail vein catheter. Thrombosis is induced five minutes after treatment by repeated external compressions of the vessel with hemostatic forceps. Two minutes post-injury, the vessel compressions are repeated and a 10 minute period of flow monitoring is started. Animals are monitored continuously for a minimum of the first ten minutes post-injury. After twenty minutes (post-injury), a flow measurement is repeated and the animals are euthanized. The section of the aorta that includes the injured section is harvested and placed in 10% formalin for possible histologic evaluation.

Example 7

In Vivo PK/PD Measurements Following Oral Administration

To evaluate the ability of these compounds to be absorbed orally and to inhibit platelet aggregation in vivo, the following experimental protocol is conducted.

Male Sprague-Dawley rats are anesthetized using an inhaled anesthetic. A cannula containing heparinized saline is introduced into the jugular vein for withdrawal of venous blood samples. Animals are allowed a 48-hour recovery period prior to dose administration.

Either compound or vehicle is administered to each animal as an oral gavage. Blood samples are taken immediately prior to compound administration, and at up to 12 time points ranging from 15 min to 24 hours following compound administration. HPLC-MS/MS is used to measure the amount of compound and/or metabolite in the blood samples.

Example 8

Inhibition of Thrombus Formation in Anesthetized Dogs

To evaluate the effect of the compounds of this invention on dynamic thrombus formation in vivo, the following experimental protocol, similar to the method of J. L. Romson et al. (*Thromb. Res.* 17:841-853, 1980), is performed.

Surgical Preparation and Instrumentation: Briefly, purpose-bred dogs are anesthetized, intubated and ventilated with room air. The heart is exposed by a left thoracotomy in the fifth intercostal space and suspended in a pericardial cradle. A 2-3 cm segment of the left circumflex coronary artery (LCCA) is isolated by blunt dissection. The artery is instrumented from proximal to distal with a flow probe, a stimulation electrode, and a Goldblatt clamp. The flow probe monitors the mean and phasic LCCA blood flow velocities. The stimulation electrode and its placement in the LCCA and the methodology to induce an occlusive coronary thrombus have been described previously (J. K. Mickelson et al., *Circulation* 81:617-627, 1990; R. J. Shebuski et al., *Circulation* 82:169-177, 1990; J. F. Tschopp et al., *Coron. Artery Dis.* 4:809-817, 1993).

Experimental Protocol: Dogs are randomized to one of four treatment protocols (n=6 per treatment group) in which the control group receives saline intravenously and the three drug-treated groups are administered compound intravenously. Upon stabilization from the surgical interventions, dogs receive either saline or compound. After approximately 30 minutes, an anodal current is applied to the LCCA for 180 min. The number and frequency of cyclic flow variations (CFV) that precede formation of an occlusive thrombus are recorded. These cyclic phenomena are caused by platelet thrombi that form in the narrowed lumen as a result of platelet aggregation (J. D. Folts et al., Circulation 54:365-370, 1976; Bush et al., Circulation 69:1161-1170, 1984). Zero flow in the LCCA for a minimum of 30 minutes indicates a lack of antithrombotic efficacy (L. G. Frederick et al., Circulation 93:129-134, 1996).

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A compound of Formula I, or its tautomer, or salt thereof:

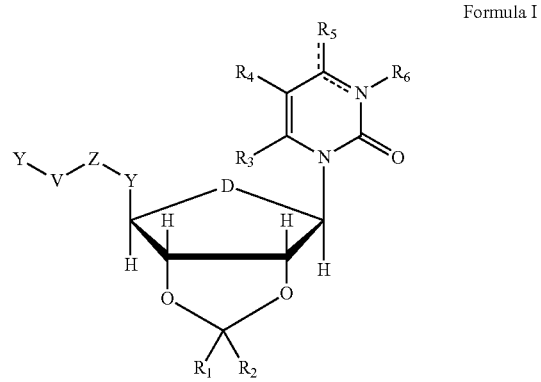

Formula I wherein:
$R_1$ and $R_2$ are each independently selected from the group consisting of: hydrogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl, aryl, heteroaryl, and saturated or unsaturated $C_{3-6}$ heterocycle; where all rings or chains optionally can bear one or more desired substituents; or $R_1$ and $R_2$ are taken together to form a ring of 3 to 7 members, with or without substitution, and with or without heteroatoms in place of ring carbon atoms;

$R_3$ and $R_4$ are independently hydrogen, alkyl, halogen, alkenyl, substituted alkenyl, alkynyl, or substituted alkynyl.

$R_5$ is —NH—CO—NHR$_8$, where R$_8$ is alkyl, cycloalkyl, alkylcycloalkyl, or aryl;

$R_6$ is absent;

D is O or $CH_2$;

V, Z, and Y are independently $CH_2$ with H optionally substituted by alkyl groups or halogens, C=O, O, S, SO, $SO_2$, or NH with H optionally substituted by an alkyl group or an acyl group; and when V and Z or Z and Y are both carbon, the linkage between the atom pair can be a saturated or unsaturated bond; or V, Z, and Y are independently absent;

X=H, —S(O)R', —S(O$_2$)R', —SO$_3$H, —S(O$_2$)NR'R", —NR'R", or —COOR', where R' and R" are independently H, a physiologically-relevant cation forming a carboxylate salt, alkyl, aryl, or aralkyl; or X is a group as provided in Formula II:

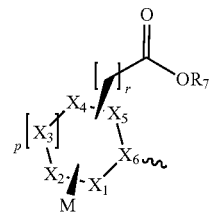

Formula II wherein:
$X_6$ is the attachment point to the moiety defined by V—Z—Y;

the ring defined by $X_1$-$X_6$ is taken to mean a ring with or without unsaturation; and $X_1$-$X_6$ are independently C, N, O, or S; and if any of $X_1$-$X_5$ is C, the carbon atom is optionally substituted with halogen, alkyl, alkoxy, or aminoalkyl; and if any of $X_1$-$X_5$ is N in an saturated ring, the nitrogen atom optionally bears substituents such as alkyl or acyl; or any of $X_1$-$X_5$ can be absent, with the proviso that at least two of $X_1$-$X_5$ are present, such that the ring described by $X_1$-$X_6$ consists of at least three atoms;

with the provisos that no two adjacent atoms $X_1$-$X_6$ are O—O or S—S and that the ring shown in Formula II contains no more than four heteroatoms, and that the shown pendant —$CO_2R_7$ unit in Formula II is a substituent on the ring described in Formula II, and that the ring of Formula II contains no halogen-group, hydroxy-group, sulfhydryl-group, or amino-group attached to an $sp^3$-hybridized-carbon atom that is bonded directly to a heteroatom selected from the group consisting of O, S, and N, as such types of compounds are unstable in many cases;

p=0, 1, or 2;

r=0 or 1;

$R_7$ is H, a physiologically-relevant cation forming a carboxylate salt, alkyl, aryl, or aralkyl; and M is H, halogen, alkyl, aminoalkyl, alkoxy, or acyl.

2. A compound of Formula Ia, or its tautomer or salt thereof:

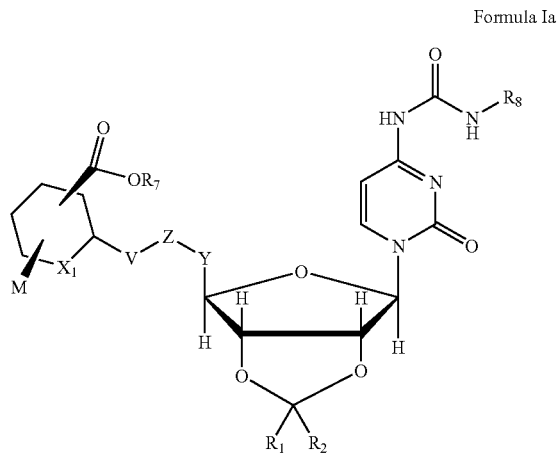

Formula Ia wherein:
the ring incorporating $X_1$ is taken to mean a saturated or unsaturated ring;
$R_1$ is aryl or aralkyl;
$R_2$ is H;
Z is O, $CH_2$, or NH;
V is $CH_2$, NH, O, $SO_2$, or C=O;
Y is $CH_2$, or C=O;
with the proviso that V or Y are not both C=O; and
if V=O, Z is not NH;
$X_1$ is CH, C—F, C—Cl, C—Br, C—$OCH_3$, C—COOH, C—$COOR_7$ or N
$R_7$ is H, a physiologically-relevant cation forming a carboxylate salt, alkyl, aryl, or aralkyl;
$R_8$ is alkyl, cycloalkyl, alkylcycloalkyl, or aryl; and
M is H, halogen, alkyl, aminoalkyl, alkoxy, or acyl.

3. The compound according to claim 2, wherein said compound is selected from the group consisting of: 2',3'-trans-cinnamylacetal-5'-(2-carboxy)benzyloxy-6-N-ethylurea cytidine (1); 2',3'-trans-cinnamylacetal-5'-(2-carboxy-6-fluoro)benzyloxy-6-N-ethylurea cytidine; 2',3'-trans-cinnamylacetal-5'-(2-carboxy-6-chloro)benzyloxy-6-N-ethylurea cytidine (2); 2',3'-trans-cinnamylacetal-5'-[2-(3-carboxy)pyridylmethyloxy]-6-N-ethylurea cytidine (4); 2',3'-trans-phenylacetal-5'-(2-carboxy)benzyloxy-6-N-ethylurea cytidine (f); 2',3'-trans-phenylacetal-5'-(2-carboxy-6-fluoro)benzyloxy-6-N-ethylurea cytidine (6); 2',3'-trans-phenylacetal-5'-(2-carboxy-6-fluoro)benzoylamino-6-N-ethylurea cytidine (7); 2',3'-trans-phenylacetal-5'-[(2-carboxy)benzylamino]carbonyl-6-N-ethylurea cytidine (8); 2',3'-trans-phenylacetal-5'-[2-(3-carboxy)pyridylmethyloxy]-6-N-ethylurea cytidine (9); 2',3'-trans-phenylacetal-5'-[2-(3-carboxy)pyridylmethyloxy]-6-N-cyclopropylurea cytidine (10); 2',3'-trans-phenylacetal-5'-(2-carboxy)benzyloxy-6-N-cyclopropylurea cytidine (11); 2',3'-trans-phenylacetal-5'-(2-carboxy-6-fluoro)benzyloxy-6-N-cyclopropylurea cytidine (12); 2',3'-trans-cinnamylacetal-5'-(2-carboxy)cyclohexylmethyloxy-6-N-ethylurea cytidine (13); 2',3'-trans-phenylacetal-5'-(2-carboxy)cyclohexylmethyloxy-6-N-ethylurea cytidine (14); and 2',3'-trans-phenylacetal-5'-(2-carboxy)cyclohexylmethyloxy-6-N-cyclopropylurea cytidine (15).

4. A compound of Formula Ib, or its tautomer or salt thereof:

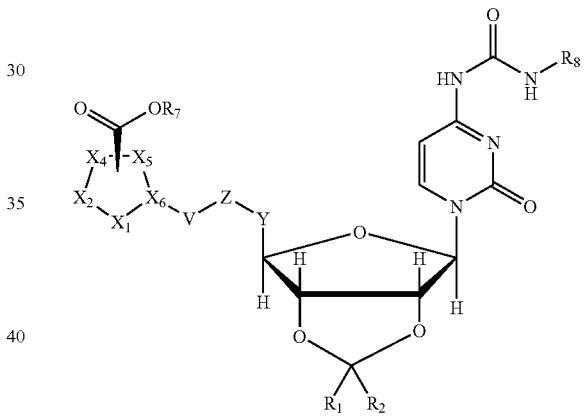

Formul Ib wherein
$R_1$ is aryl or aralkyl;
$R_2$ is H;
$R_7$ is H, a physiologically-relevant cation forming a carboxylate salt, alkyl, aryl, or aralkyl;
$R_8$ is alkyl, cycloalkyl, alkylcycloalkyl, or aryl;
$X_1$, $X_2$, $X_4$, $X_5$, and $X_6$ are taken to mean a ring with or without unsaturation and are independently selected from the group consisting of: N, C, S, or O; and $X_1$-$X_6$ are taken to mean a ring of from three to five atoms;
V is NH, $CH_2$, or C=O;
Y is $CH_2$ or C=O; and
Z is O, $CH_2$, NH, S or $SO_2$.

5. The compound according to claim 4, wherein said compound is selected from the group consisting of: 2',3'-trans-cinnamylacetal-5'-[2-(3-carboxy)furanylmethyloxy]-6-N-ethylurea cytidine (16); 2',3'-trans-cinnamylacetal-5'-[2-(3-carboxy)thiophenenylmethyloxy]-6-N-ethylurea cytidine (17); 2',3'-trans-cinnamylacetal-5'-[2-(3-carboxy)furanylmethyloxy]-6-N-cyclopropylurea cytidine (18); 2',3'-trans-cinnamylacetal-5'-[2-carboxy)cyclopentylmethyloxy]-6-N-ethylurea cytidine (19); 2',3'-trans-cinnamylacetal-5'-(2-carboxy)cyclopentylmethyloxy-6-N-cyclopropylurea cytidine (20); 2',3'-trans-phenylacetal-5'-[2-(3-carboxy)furanylmethyloxy]-6-N-ethylurea cytidine (21); 2',3'-trans-phenylacetal-5'-[2-(3-carboxy)thiophenenylmethyloxy]-6-N-cyclopropylurea cytidine (22); 2',3'-trans-phenylacetal-5'-[2-(3-carboxy)thiophenenylmethyloxy]-6-N-ethylurea cytidine (23); 2',3'-trans-phenylacetal-5'-(2-carboxy)cyclopentylmethyloxy-6-N-ethylurea cytidine (24); 2',3'-trans-phenylacetal-5'-(2-carboxy)cyclopentylmethyloxy-6-N-cyclopropylurea cytidine (25); 2',3'-trans-phenylacetal-5'-(2-carboxy)cyclopropylmethyloxy-6-N-ethylurea cytidine (26); and 2',3'-trans-cinnamylacetal-5'-(2-carboxy)cyclopropylmethyloxy-6-N-ethylurea cytidine (27).

6. A compound of Formula Ic, or its tautomer or salt thereof:

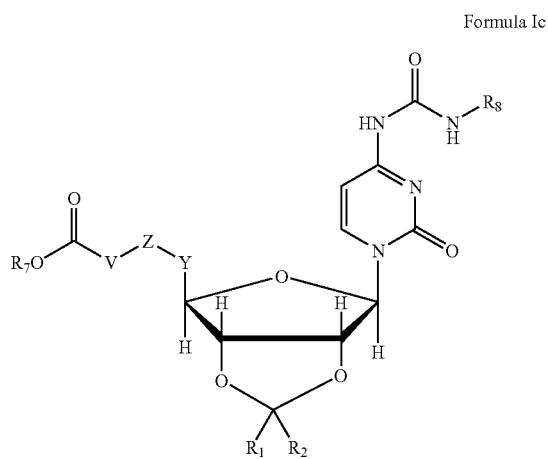

Formula Ic wherein:
R$_1$ is aryl or aralkyl;
R$_2$ is H;
R$_7$ is H, a physiologically-relevant cation forming a carboxylate salt, alkyl, aryl, or aralkyl;
R$_8$ is alkyl, cycloalkyl, alkylcycloalkyl, or aryl;
V is CH$_2$, NH, or O;
Z is O, CH$_2$, C=O, NH, S, SO, or SO$_2$; or
V and Z are absent; and
Y is CH$_2$, or C=O,
with the proviso that both Z and Y are not C=O.

7. The compound according to claim 6, wherein said compound is selected from the group consisting of: 2',3'-trans-cinnamylacetal-5'-(2-carboxy)methyleno-6-N-ethylurea cytidine (28); 2',3'-trans-cinnamylacetal-5'-(2-carboxy)methyloxy-6-N-ethylurea cytidine (29); 2',3'-trans-cinnamylacetal-5'-(2-carboxy)methylamino-6-N-ethylurea cytidine (30); 2',3'-trans-phenylacetal-5'-(2-carboxy)methyleno-6-N-ethylurea cytidine (31); 2',3'-trans-phenylacetal-5'-(2-carboxy)methyloxy-6-N-ethylurea cytidine (32); and 2',3'-trans-phenylacetal-5'-(2 carboxy)methylamino-6-N-ethylurea cytidine (33).

8. A pharmaceutical formulation comprises the compound according to claim 1 and a pharmaceutically acceptable carrier.

9. A pharmaceutical formulation comprises the compound according to claim 2 and a pharmaceutically acceptable carrier.

10. A pharmaceutical formulation comprises the compound according to claim 3 and a pharmaceutically acceptable carrier.

11. A pharmaceutical formulation comprises the compound according to claim 4 and a pharmaceutically acceptable carrier.

12. A pharmaceutical formulation comprises the compound according to claim 5 and a pharmaceutically acceptable carrier.

13. A pharmaceutical formulation comprises the compound according to claim 6 and a pharmaceutically acceptable carrier.

14. A pharmaceutical formulation comprises the compound according to claim 7 and a pharmaceutically acceptable carrier.

15. A method of treating thrombosis comprising:
administering to a subject in need thereof a therapeutically effective amount of a compound according to claim 1, wherein said amount is effective to inhibit platelet aggregation in the subject.

16. A method of treating thrombosis comprising:
administering to a subject in need thereof a therapeutically effective amount of a compound according to claim 2, wherein said amount is effective to inhibit platelet aggregation in the subject.

17. A method of treating thrombosis comprising:
administering to a subject in need thereof a therapeutically effective amount of a compound according to claim 3, wherein said amount is effective to inhibit platelet aggregation in the subject.

18. A method of treating thrombosis comprising:
administering to a subject in need thereof a therapeutically effective amount of a compound according to claim 4, wherein said amount is effective to inhibit platelet aggregation in the subject.

19. A method of treating thrombosis comprising:
administering to a subject in need thereof a therapeutically effective amount of a compound according to claim 5, wherein said amount is effective to inhibit platelet aggregation in the subject.

20. A method of treating thrombosis comprising:
administering to a subject in need thereof a therapeutically effective amount of a compound according to claim 6, wherein said amount is effective to inhibit platelet aggregation in the subject.

21. A method of treating thrombosis comprising:
administering to a subject in need thereof a therapeutically effective amount of a compound according to claim 7, wherein said amount is effective to inhibit platelet aggregation in the subject.

22. A method for inhibiting platelet aggregation in blood or a blood product, comprising:
administering to blood or a blood product an effective amount of a compound according to claim 1, wherein said amount is effective to inhibit platelet aggregation in the blood or the blood product.

* * * * *